US009302977B2

(12) United States Patent
Raillard et al.

(10) Patent No.: US 9,302,977 B2
(45) Date of Patent: Apr. 5, 2016

(54) METHOD OF MAKING MONOMETHYL FUMARATE

(71) Applicant: XenoPort, Inc., Santa Clara, CA (US)

(72) Inventors: Stephen P. Raillard, Mountain View, CA (US); Randall A. Scheuerman, Santa Clara, CA (US); Suresh K. Manthati, Sunnyvale, CA (US)

(73) Assignee: XenoPort, Inc., Santa Clara, CA (US)

( * ) Notice: Subject to any disclaimer, the term of this patent is extended or adjusted under 35 U.S.C. 154(b) by 17 days.

(21) Appl. No.: 14/298,713

(22) Filed: Jun. 6, 2014

(65) Prior Publication Data

US 2014/0364604 A1 Dec. 11, 2014

Related U.S. Application Data

(60) Provisional application No. 61/832,665, filed on Jun. 7, 2013.

(51) Int. Cl.
*C07D 295/185* (2006.01)
*C07C 67/08* (2006.01)
*C07C 67/333* (2006.01)
*C07C 67/14* (2006.01)
*C07C 231/12* (2006.01)

(52) U.S. Cl.
CPC ............... *C07C 67/14* (2013.01); *C07C 67/08* (2013.01); *C07C 67/333* (2013.01); *C07C 231/12* (2013.01); *C07D 295/185* (2013.01)

(58) Field of Classification Search
CPC ....................................... C07C 67/14
See application file for complete search history.

(56) References Cited

U.S. PATENT DOCUMENTS

| | | | |
|---|---|---|---|
| 3,139,395 A | 6/1964 | Griffin | |
| 3,336,364 A | 8/1967 | Dill | |
| 4,851,439 A | 7/1989 | Speiser et al. | |
| 4,863,916 A | 9/1989 | Habich et al. | |
| 4,959,389 A | 9/1990 | Speiser et al. | |
| 5,073,641 A | 12/1991 | Bundgaard et al. | |
| 5,145,684 A | 9/1992 | Liversidge et al. | |
| 5,149,695 A | 9/1992 | Speiser et al. | |
| 5,424,332 A | 6/1995 | Speiser et al. | |
| 5,451,667 A | 9/1995 | Speiser et al. | |
| 5,534,250 A | 7/1996 | Klaveness et al. | |
| 6,130,248 A | 10/2000 | Nudelman et al. | |
| 6,277,882 B1 | 8/2001 | Joshi et al. | |
| 6,355,676 B1 | 3/2002 | Joshi et al. | |
| 6,359,003 B1 | 3/2002 | Joshi et al. | |
| 6,379,697 B1 | 4/2002 | Gregoriadis et al. | |
| 6,436,992 B1 | 8/2002 | Joshi et al. | |
| 6,509,376 B1 | 1/2003 | Joshi et al. | |
| 6,613,800 B1 | 9/2003 | Smith | |
| 6,709,868 B2 | 3/2004 | Law et al. | |
| 6,723,508 B2 | 4/2004 | Sprenger et al. | |
| 6,858,750 B2 | 2/2005 | Joshi et al. | |
| 7,157,423 B2 | 1/2007 | Joshi et al. | |
| 7,320,999 B2 | 1/2008 | Joshi et al. | |
| 7,432,240 B2 | 10/2008 | Joshi et al. | |
| 7,612,110 B2 | 11/2009 | Joshi et al. | |
| 7,619,001 B2 | 11/2009 | Joshi et al. | |
| 7,638,118 B2 | 12/2009 | Flachsmann et al. | |
| 7,790,916 B2 | 9/2010 | Joshi et al. | |
| 7,803,840 B2 | 9/2010 | Joshi et al. | |
| 7,906,659 B2 | 3/2011 | Joshi et al. | |
| 7,915,310 B2 | 3/2011 | Joshi et al. | |
| 8,067,467 B2 | 11/2011 | Joshi et al. | |
| 8,148,414 B2 | 4/2012 | Gangakhedkar et al. | |
| 8,399,514 B2 | 3/2013 | Lukashev et al. | |
| 8,524,773 B2 | 9/2013 | Joshi et al. | |
| 8,669,281 B1 | 3/2014 | Zeidan et al. | |
| 8,759,393 B2 | 6/2014 | Joshi et al. | |
| 8,778,991 B2 | 7/2014 | Gangakhedkar et al. | |
| 8,785,443 B2 | 7/2014 | Gangakhedkar et al. | |
| 8,906,420 B2 | 12/2014 | Nilsson et al. | |
| 8,952,006 B2 | 2/2015 | Cundy et al. | |
| 2003/0018072 A1 | 1/2003 | Joshi et al. | |
| 2004/0054001 A1 | 3/2004 | Joshi et al. | |
| 2004/0102525 A1 | 5/2004 | Kozachuk | |
| 2005/0095292 A1 | 5/2005 | Benjamin et al. | |
| 2005/0096369 A1 | 5/2005 | Hoang | |
| 2005/0101779 A1 | 5/2005 | Sagi et al. | |
| 2005/0148664 A1 | 7/2005 | Joshi et al. | |
| 2006/0205659 A1 | 9/2006 | Joshi et al. | |

(Continued)

FOREIGN PATENT DOCUMENTS

| | | |
|---|---|---|
| CN | 1616400 A | 5/2005 |
| CN | 101318901 | 12/2008 |

(Continued)

OTHER PUBLICATIONS

Altmeyer et al., Antipsoriatic effect of fumaric acid derivatives, J. Amer. Acad. Derm. (1994), 30(6): 977-981.

Altschul et al., "Gapped BLAST and PSI-BLAST: a new generation of protein database search programs," Nucleic Acids Research, 1997, vol. 25, No. 17, pp. 3389-3402.

Ashe, Learning and memory in transgenic mice modeling Alzheimer's disease. Learning & Memory (2001), 8, 301-308.

Associated Press; FDA mulls drug to slow late-stage Alzheimer's [online]; [retrieved on Sep. 24, 2003]; retrieved from the internet, <http://www.cnn.com/2003/HEALTH/conditions/09/24/alzheimers.drug.ap/index.html>; Sep. 24, 2003; 2 pages.

(Continued)

*Primary Examiner* — Paul A Zucker
(74) *Attorney, Agent, or Firm* — Polsinelli PC

(57) ABSTRACT

Methods of making monomethyl fumarate, which can then also be used in methods of making prodrugs of monomethyl fumarate, are disclosed. Monomethyl fumarate and prodrugs of monomethyl fumarate are useful for treating neurodegenerative, inflammatory, and autoimmune diseases including multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

39 Claims, No Drawings

(56) References Cited

U.S. PATENT DOCUMENTS

| | | |
|---|---|---|
| 2006/0269925 A1 | 11/2006 | Nunes et al. |
| 2007/0009475 A1 | 1/2007 | Flachsmann et al. |
| 2007/0027076 A1 | 2/2007 | Joshi et al. |
| 2007/0213300 A1 | 9/2007 | Liu et al. |
| 2007/0231382 A1 | 10/2007 | Karnachi et al. |
| 2007/0248663 A1 | 10/2007 | Joshi et al. |
| 2007/0253902 A1 | 11/2007 | Lobb et al. |
| 2008/0004344 A1 | 1/2008 | Nilsson et al. |
| 2008/0033199 A1 | 2/2008 | Lai et al. |
| 2008/0089861 A1 | 4/2008 | Went et al. |
| 2008/0089896 A1 | 4/2008 | Wang et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0048651 A1 | 2/2010 | Gangakhedkar et al. |
| 2010/0099907 A1 | 4/2010 | Raillard et al. |
| 2010/0105784 A1 | 4/2010 | Remon et al. |
| 2010/0130607 A1 | 5/2010 | Gold |
| 2010/0144651 A1 | 6/2010 | Nilsson et al. |
| 2010/0226981 A1 | 9/2010 | Karaborni et al. |
| 2010/0260755 A1 | 10/2010 | Gammans et al. |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0034274 A1 | 2/2012 | Nilsson et al. |
| 2012/0034303 A1 | 2/2012 | Nilsson et al. |
| 2012/0095003 A1 | 4/2012 | Gangakhedkar et al. |
| 2012/0157523 A1 | 6/2012 | Gangakhedkar et al. |
| 2012/0165404 A1 | 6/2012 | Lukashev |
| 2013/0065909 A1 | 3/2013 | Milne et al. |
| 2013/0172391 A1 | 7/2013 | Kahrs |
| 2013/0203753 A1 | 8/2013 | Cundy et al. |
| 2013/0259856 A1 | 10/2013 | Kaye |
| 2013/0259906 A1 | 10/2013 | Joshi et al. |
| 2013/0295169 A1 | 11/2013 | Goldman et al. |
| 2013/0302410 A1 | 11/2013 | Gold |
| 2013/0317103 A1 | 11/2013 | Lukashev |
| 2013/0324539 A1 | 12/2013 | Virsik et al. |
| 2014/0051705 A1 | 2/2014 | Cundy et al. |
| 2014/0056973 A1 | 2/2014 | Ma et al. |
| 2014/0056978 A1 | 2/2014 | Karaborni et al. |
| 2014/0057917 A1 | 2/2014 | Cundy et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179778 A1 | 6/2014 | Mao et al. |
| 2014/0179779 A1 | 6/2014 | Chao |
| 2014/0193386 A1 | 7/2014 | Preiss-Bloom et al. |
| 2014/0193387 A1 | 7/2014 | Gruskin et al. |
| 2014/0193388 A1 | 7/2014 | Velders et al. |
| 2014/0193390 A1 | 7/2014 | Valenzano et al. |
| 2014/0193392 A1 | 7/2014 | Annunziata et al. |
| 2014/0193393 A1 | 7/2014 | Gulati |
| 2014/0193495 A1 | 7/2014 | Nilsson |
| 2014/0194427 A1 | 7/2014 | Chao |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275250 A1 | 9/2014 | Cundy et al. |
| 2014/0284245 A1 | 9/2014 | Karaborni et al. |
| 2014/0323570 A1 | 10/2014 | Gold |
| 2014/0329818 A1 | 11/2014 | Gangakhedkar et al. |
| 2014/0336151 A1 | 11/2014 | Chao |
| 2014/0378542 A1 | 12/2014 | Mao et al. |
| 2015/0038499 A1 | 2/2015 | Virsik |
| 2015/0073049 A1 | 3/2015 | Mao et al. |
| 2015/0079180 A1 | 3/2015 | Karaborni et al. |
| 2015/0190360 A1 | 7/2015 | Cundy |
| 2015/0265707 A1 | 9/2015 | Manthati et al. |

FOREIGN PATENT DOCUMENTS

| | | | |
|---|---|---|---|
| CN | 101774913 A | | 7/2010 |
| DE | 1165586 B | * | 7/1961 |
| DE | 1165586 | | 3/1964 |
| DE | 10360869 A1 | | 4/2005 |
| EP | 2692344 A1 | | 2/2014 |
| GB | 1153927 A | | 6/1969 |
| GB | 1404989 A | | 9/1975 |
| GB | 2285805 A | | 7/1995 |
| JP | S60181047 A | | 9/1985 |
| JP | H03294245 A | | 12/1991 |
| JP | 2001158760 A | | 6/2001 |
| PL | 153592 | | 10/1991 |
| WO | WO 96/36613 | | 11/1996 |
| WO | WO 98/29114 | | 7/1998 |
| WO | 98/52549 | | 11/1998 |
| WO | 99/49858 | | 10/1999 |
| WO | WO 99/51191 A1 | | 10/1999 |
| WO | WO 99/62973 A1 | | 12/1999 |
| WO | WO 00/10560 A1 | | 3/2000 |
| WO | WO 00/12072 A2 | | 3/2000 |
| WO | 02/055063 A2 | | 7/2002 |
| WO | 02/055066 A1 | | 7/2002 |
| WO | WO 02/055067 | | 7/2002 |
| WO | 03/087174 A2 | | 10/2003 |
| WO | 2005/023241 A1 | | 3/2005 |
| WO | 2005/027899 A1 | | 3/2005 |
| WO | 2006/037342 A2 | | 4/2006 |
| WO | WO 2006/050730 | | 5/2006 |
| WO | 2006/122652 A2 | | 11/2006 |
| WO | WO 2007/006307 | | 1/2007 |
| WO | WO 2007/006308 | | 1/2007 |
| WO | 2007/042034 A1 | | 4/2007 |
| WO | WO 2007/042035 | | 4/2007 |
| WO | WO 2008/096271 | | 8/2008 |
| WO | WO 2008/097596 | | 8/2008 |
| WO | WO 2010/022177 | | 2/2010 |
| WO | WO 2010/079221 | | 7/2010 |
| WO | WO 2010/079222 | | 7/2010 |
| WO | WO 2010/126605 | | 11/2010 |
| WO | WO 2011/080344 | | 7/2011 |
| WO | WO 2012/162669 | | 11/2012 |
| WO | 2012/170923 A1 | | 12/2012 |
| WO | WO 2013/022882 | | 2/2013 |
| WO | WO 2013/076216 | | 5/2013 |
| WO | WO 2013/119677 | | 8/2013 |
| WO | WO 2013/119791 | | 8/2013 |
| WO | WO 2014/031894 | | 2/2014 |
| WO | WO 2014/031897 | | 2/2014 |
| WO | WO 2014/071371 | | 5/2014 |
| WO | WO 2014/096425 | | 6/2014 |
| WO | WO 2014/100728 | | 6/2014 |
| WO | WO 2014/190056 | | 11/2014 |
| WO | WO 2015/028472 | | 3/2015 |
| WO | WO 2015/028473 | | 3/2015 |

OTHER PUBLICATIONS

Author Unknown, BG 00012, BG 12/oral fumarate, FAG-201, second-generation fumarate derivative—Fumapharm/Biogen Idec, Drugs RD (2005), 6(4): 229-230.

Bar-Or et al., "Clinical efficacy of BG-12 (dimethyl fumarate) in patients with relapsing-remitting multiple sclerosis: subgroup analyses of the DEFINE study," J. Neurol, 2013, vol. 260, pp. 2297-2305.

Bardgett et al., NMDA receptor blockade and hippocampal neuronal loss impair fear conditioning and position habit reversal in C57B1/6 mice. Brain Res Bull (2003), 60, 131-142.

Behari et al., Baseline characteristics of a subpopulation of Indian patients enrolled in two phase 3 trials for oral BG-12 in relapsing-remitting multiple sclerosis, 62nd Ann Mtg. Amer. Acad. Neurol. (2010), poster, 2 pages.

Benoit et al., Etude Clinique de L'ester B-Morpholinoethylique de L'Acide Niflumique en Stomatologie Infantile, Rev. Odontostomatol Midi Fr. (1975), 4: 249-261.

(56) References Cited

OTHER PUBLICATIONS

Bertone, "Prevalence of Gastric Ulcers in Elite, Heavy Use Western Performance Horses," AAEP Proceedings (2000). 46: 256-259.
Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic in the human skin-severe, combined immunodeficient mouse transplant model. J Pharmacol Expt'l Therapeutics (2008), 324(3), 938-947.
Blad, et al., "Biological and Pharmacological Roles of HCA Receptors", Advances in Pharmacology, 2011, 62: 219-250.
Boehncke, "Animal Models of T Cell-Mediated Skin Diseases, Chapter 12: The Psoriasis SCID Mouse Model: A Tool for Drug Discovery?" Ernst Schering Res Found Workshop 50, Zollner et al., eds. New York: Springer (2005) pp. 213-234.
Brown et al., "Goodman & Gilman's The Pharmacological Basis of Therapeutics, Tenth Edition: Chapter 7, Muscarinic Receptor Agonists and Antagonists," A. Gilman, J. Hardman and L. Limbird, eds., Mc-Graw Hill Press, 2001, pp. 155-173.
Bruhn et al., "Concordance between enzyme activity and genotype of glutathione S-transferase theta (GSTT1)," Biochemical Pharmacology, 1998, vol. 56, pp. 1189-1193.
Bundgaard et al., Esters of N,N-Disubstituted 2-Hydroxyacetamides as a Novel Highly Biolabile Prodrug Type for Carboxylic Acid Agents, J. Med. Chem. (1987), 30(3): 451-454.
Bundgaard et al., Glycolamide esters as a novel biolabile prodrug type for non-steroidal anti-inflammatory carboxylic acid drugs, Int. J. Pharm. (1988) 43: 101-110.
Büyükcoskun, Central Effects of Glucagon-like Peptide-1 on Cold Restraint Stress-induced Gastric Mucosal Lesions, Turk J. Gastroenterol (2007), 18(3): 150-156.
Büyükcoskun, Role of Intracerebroventricular Vasopressin in the Development of Stress-Induced Gastric Lesions in Rats, Physiol. Res. (1999), 48: 451-455.
Caira, "Crystalline Polymorphism of Organic Compounds," Topics in Current Chemistry, Springer, Berlin, DE (1998), vol. 198, pp. 163-208.
Capello, et al., "Marburg type and Balo's concentric sclerosis: Rare and acute variants of multiple sclerosis", Neurological Sciences 200411 IT, vol. 25, No. Suppl. 4, Nov. 2004, pp. S361-S363.
Cavarra et al., Effects of cigarette smoke in mice with different levels of α1-proteinase inhibitor and sensitivity to oxidants. Am J Respir Crit Care Med (2001), 164, 886-890.
Champion, et al., "Flushing and Flushing Syndromes, Rosacea and Perioral Dermatitis", Rook Wilkinson Ebling Textbook of Dermatology, 6th ed. vol. 3, Oxford, UK: Blackwell Scientific, 1998, pp. 2099-2104.
Chaudhary et al., "Enhancement of solubilization and bioavailability of poorly soluble drugs by physical and chemical modifications: A recent review," Journal of Advanced Pharmacy Education & Research (2012), 2(1), pp. 32-67.
Chen et al., "Nanonization strategies for poorly water-soluble drugs," Drug Discovery Today, 2010, pp. 1-7.
Cockcroft et al., Bronchial reactivity to inhaled histamine: a method and clinical survey. Clin Allergy (1977), 7, 235-243.
Cross, et al. Dimethyl Fumarate, an Immune Modulator and Inducer of the Antioxidant Response, Suppresses HIV Replication and Macrophage-Mediated Neurotoxicity: A Novel Candidate for HIV Neuroprotection. The Journal of Immunology, (2011), 187(10): 5015-5025.
Damasio; "Alzheimer's Disease and Related Dementias;" Cecil Textbook of Medicine; 1996; 20th Edition, vol. 2; pp. 1992-1996.
De Jong et al., Selective stimulation of T helper 2 cytokine responses by the anti-psoriasis agent monomethylfumarate, Eur. J. Immunol. (1996), 26: 2067-2074.
Dibbert, et al.,: "Detection of fumarate-glutathione adducts in the portal vein blood of rats: Evidence for rapid dimethyl fumarate metabolism", Archives of Dermatological Research 2013 Springer Verlag Deu, vol. 305, No. 5, Jul. 2013, pp. 447-451.
Eberle, et al. Fumaric Acid Esters in Severe Ulcerative Necrobiosis Lipoidica: A Case Report and Evaluation of Current Therapies. Acta Dermato-Venereologica (2010) 90(1): 104-106.
Ellrichmann et al., Efficacy of fumaric acid esters in the R6/2 and YAC128 models of Huntington's disease, PLOS One (2011), 6(1): 11 pages.
Etter et al., "The Use of Cocrystallization as a Method of studying Hydrogen Bond Preferences of 2-Aminopyrimidine," Journal of the Chemical Society (1990), No. 8, pp. 589-591.
Etter et al., "Graph Set Analysis of Hydrobgen-Bond Patterns in Organic Crystals," Acta Crystallogr., Sect. B, Struct. Sci. (1990), B46, pp. 256-262.
Etter et al., "Hydrogen Bond Directed Cocrystallization and Molecular Recognition Properties of Diarylureas," Journal of the Chemical Society (1990), No. 112, pp. 8415-8426.
Eugster et al., Superantigen overcomes resistance of IL-6 deficient mice towards MOG-induced EAE by a TNFR1 controlled pathway. Eur J Immunol (2001), 31, 2302-2312.
European Commission Health & Consumer Protection Directorate-General, Report of the scientific committee on animal nutrition on the safety of fumaric acid, adopted Jan. 22, 2003: 18 pages.
Feinstein et al., Anti-inflammatory and prometabolic effects of BG-12 in glial cells, 26th Congress Eur. Cmtee. Treat. Res. Mult. Scler. (2010), poster: 1 page.
Fits et al., Imiquimod-Induced Psoriasis-Like Skin Inflammation in Mice Is Mediated via the IL-23/IL-17 Axis, J. Immunol. (2009), 182: 5836-5845.
Food and Drug Administration—Department of Health and Human Services; "International Conference on Harmonisation; Guidelines for the Photostability Testing of New Drug Substances and Products; Availability; Notice," Federal Register, vol. 62, No. 95; May 16, 1997, pp. 27115-27122.
Fox et al., Baseline characteristics of patients in a randomized, multicenter, placebo-controlled and active comparator trial evaluating efficacy and safety of BG-12 in relapsing-remitting multiple sclerosis: the CONFIRM trial, 62nd Ann Mtg. Amer. Acad. Neurol. (2010), poster, 2 pages.
Fox et al., Placebo-controlled phase 3 study of oral BG-12 or glatiramer in multiple sclerosis, N Engl J Med. Sep. 20, 2012;367(12):1087-97. Erratum in: N Engl J Med. Oct. 25, 2012;367(17):1673.
Frycak et al., Evidence of covalent interaction of fumaric acid esters with sulfhydryl groups in peptides, J. Mass. Spectrom. (2005), 40: 1309-1318.
Gadad et al., Synthesis, spectral studies and anti-inflammatory activity of glycolamide esters of niflumic acid as potential prodrugs, Arzneim Forsch Drug Res. (2002), 52(11): 817-821.
Gambichler, et al. Clearance of Necrobiosis lipoidica with Fumaric Acid Esters. Dermatology (2003), 207(4): 422-424.
Goke et al., Effect of a Specific Serine Protease Inhibitor on the Rat Pancreas: Systemic Administration of Camostate and Exocrine Pancreatic Secretion, Digestion (1984) 30: 171-178.
Gogas et al., Comparison of the efficacy and tolerability of a novel methyl hydrogen fumarate prodrug with dimethyl fumarate in rodent EAE and GI irritation models, XenoPort, Inc.; 26th Congress of the European Committee for Treatment and Research in Multiple Sclerosis (ECTRIMS), 2010 (Poster #671), 1 page.
Gold et al., Baseline characteristics of patients in the DEFINE trial: a randomized, multicenter, double blind, placebo-controlled, phase 3 study of BG-12 in relapsing-remitting multiple sclerosis, 62nd Ann Mtg. Amer. Acad. Neurol. (2010), poster, 2 pages.
Gold et al., Placebo-controlled phase 3 study of oral BG-12 for relapsing multiple sclerosis, N Engl J Med. Sep. 20, 2012;367(12):1098-107, Erratum in: N Engl J Med. Dec. 13, 2012;367(24):2362.
Gorbitz et al., "On the inclusion of solvent molecules in the crystal structures of organic compounds," Acta Cryst. (2000), B56, pp. 526-534.
Ghoreschi Kamran, et al., "Furmarates improve psoriasis and multiple sclerosis by inducing type II dendritic cells", The Journal of Experimental Medicine, Rockefeller University Press, US, vol. 208, No. 11, Oct. 24, 2011, pp. 2291-2303.

(56) References Cited

OTHER PUBLICATIONS

Griffin, et al., The Chemistry of Photodimers of Maleic and Fumaric Acid Derivatives. I. Dimethyl Fumarate Dimer; J. Am. Chem. Soc. (1961), 83: pp. 2725-2728.
Grigorian et al., Control of T-cell mediated autoimmunity by metabolite flux to N-glycan biosynthesis, J. Bio. Chem. (2007), 282(27): 20027-20035.
Guenther, et al., Macular Exanthema Due to Fumaric Acid Esters. Annals of Pharmacotherapy (2003), 37(2): 234-236.
Gurney et al., Motor neuron degeneration in mice that express a human Cu,Zn superoxide dismutase mutation. Science (1994), 264, 1772-1775.
Hanson et al., Nicotinic acid- and monomethyl funarate-induced flushing involves GPR109A expressed by keratinocytes and COX-2-dependent prostanoid formation in mice, J. Clin. Invest. (2010), 120(8): 2910-2919.
Heiligenhaus, et al. Influence of dimethylfumarate on experimental HSV-1 necrotizing keratitis. Graefe's Archive for Clinical and Experimental Ophthalmology (2004), 242(10): 870-877.
Heiligenhaus, et al. Improvement of herpetic stromal keratitis with fumaric acid derivate is associated with systemic induction of T helper 2 cytokines. Clinical and Experimental Immunology (2011), 142(1): 180-187.
Hiraku et al., Absorption and Excretion of Camostat Orally Administered to Male Rabbit and Healthy Subject, Iyakuhin Kenkyu (1982) 13(3): 756-765.
Horig et al., From bench to clinic and back: Perspective on the 1st IQPC Translational Research Conference, J. Transl. Med. (2004), 2(44), 8 pages.
Hoxtermann et al., Fumaric acid esters suppress peripheral CD4- and CD8- positive lymphocytes in psoriasis, Dermatology (1998), 196: 223-230.
Hurd et al., Vinylation and the Formation of Acylals:, J. Am. Chem. Soc.; vol. 78; Jan. 5, 1956; pp. 104-106.
Iyer et al., Synthesis of iodoalkylacylates and their use in the preparation of S-alkyl phosphorothiolates. Synth Commun (1995), 25(18), 2739-2749.
Jamil, et al., "Studies of Photostability of Reserpine in Parenteral Solutions," Die Pharmazie (1983), 38: pp. 467-469.
Jennings, Squamous cell carcinoma as a complication of fumaric acid ester immunosuppression, J. Eur. Acad. Dermatol. Venereol. (2009), DOI: 10.1111/j.1468-3083.2009.03234.x, 1 page.
Jurjus et al., Animal models of inflammatory bowel disease. J Pharmacol Toxicol Methods (2004), 50, 81-92.
Kappos et al., Efficacy and safety of oral fumarate in patients relapsing-remitting multiple sclerosis: a multicentre, randomised, double-blind, placebo controlled phase llb study, Lancet (2008), 372: 1463-1472.
Kamimura et al., "Stereoselective formation of optically active 2-oxy-1,3-oxazolidin-4-ones from chiral O-acylmandelamides or lactamides", Tetrahedron 58, 2002, 8763-8770.
Khan et al., Synthesis and biological evaluation of glycolamide esters as potential prodrugs of some non-steroidal anti-inflammatory drugs, Ind. J. Chem. (2002) 41B: 2172-2175.
Killestein, et al., "Oral treatment for multiple sclerosis," Lancet Neurology, Lancet Publishing Group, London, GB, vol. 10, No. 11, Nov. 2011, pp. 1026-1034.
Klein, et al. Off-label use of fumarate therapy for granulomatous and inflammatory skin diseases other than psoriasis vulgaris: a retrospective study. (2012), Journal of the European Academy of Dermatology and venereology (2012), 26(11): 1400-1406 (also on-line ref: Klein, et al., (2011), J Eur Acad Dermatol Venereol doi: 10.1111/j.1468-3083.2011.04303.x).
Kreuter et al., Fumaric acid esters in necrobiosis lipoidica: results of a prospective noncontrolled study. British Journal of Dermatology (2005) 153(4): 802-807.
Kumar et al., "Molecular Complexes of Some Mono- and Dicarboxylic Acids with trans-1,4-Dithiane-1,4-dioxide," American Chemical Society, Crystal Growth & Design (2002), 2(4), pp. 313-318.

Layzer; "Section Five—Degenerative Diseases of the Nervous System"; Cecil Textbook of Medicine; 1996; 20th Edition, vol. 2; pp. 2050-2057.
Lee et al., Spotlight on fumarates, Int. MS J. (2008), 15: 12-18.
Linker et al., Identification and development of new therapeutics for multiple sclerosis, Treds. Pharm. Sci. (2008), DOI 10.1016/j.tips.2008.07.012, 8 pages.
Linker et al., Fumaric acid esters exert neuroprotective effects in neuroinflammation via activation of the Nrf2 antioxidant pathway, Brain (2011), 134: 678-692.
Litjens e al., Monomethylfumarate affects polarization of monocyte-derived dendritic cells resulting in down-regulated Th1 lymphocyte responses, Eur. J. Immunol. (2004), 34: 565-575.
Litjens et al., Pharmacokinetics of oral fumarates in healthy subjects, Br. J. Clin. Pharmacol. (2004), 58(4): 429-432.
Litjens et al., Effects of monomethylfumarate on dendritic cell differentiation, Br. J. Dermatol. (2006), 154: 211-217.
Loewe et al., Dimethylfumarate impairs melanoma growth in metastasis, Cancer Res. (2006), 66(24): 11888-11896.
Lopez-Diego et al., Novel therapeutic strategies for multiple sclerosis—a multifaceted adversary, Nat. Review. Drug Disc. (2008), 7:909-925.
Los et al., Nuevos Estered De Acidos Anilinonicotinicos Y N-Fenilantranilicos Sustituidos, II Farmaco—Ed. Sc. (1980), 36(5): 372-85.
Lukashev et al., Activation of Nrf2 and modulation of disease by BG00012 (dimethyl fumarate) suggest a dual cytoprotective and anti-inflammatory mechanism of action, 62nd Ann Mtg. Amer. Acad. Neurol. (2010), poster, 4 pages.
Mandhane, et al., Adenosine A2 receptors modulate haloperidol-induced catalepsy in rats. Eur. J. Pharmacol (1997), 328, 135-141.
Martorana et al., Roflumilast fully prevents emphysema in mice chronically exposed to cigarette smoke. Am J Respir Crit Care Med (2005), 172, 848-853.
Meissner et al., "Dimethyl fumarate—only an anti-psoriatic medication?", Journal Der Deutschen Demrmatologischen Gesellschaft (2012), vol. 10, pp. 793-801.
Menter et al., Guidelines of care for the management of psoriasis and psoriatic arthritis, J. Am. Acad. Dermatol. (2009), doi:10.1016/j.jaad.2009.03.027, 35 pages.
Merisko-Liversidge et al., "Nanosizing: a formulation approach for poorly-water-soluble compounds," European Journal of Pharmaceutical Sciences, 18 (2003), pp. 113-120.
Miller et al., Experimental Autoimmune Encephalomyelitis in the Mouse, Current Protocols in Immunology (2007), Supp. 78: 15.1.1-15.1.18.
Milo, et al., "Combination therapy in multiple sclerosis", Journal of Neuroimmunology, vol. 231, No. 1, 2011, pp. 23-31.
Mosmann et al., TH1 and TH2 cells: different patterns of lymphokine secretion lead to different functional properties, Ann. Rev. Immunol. (1989), 7: 145-73.
Mrowietz, et al., "Treatment of Psoriasis with Fumaric Acid Esters: Results of a prospective Multicenter Study," British Journal of Dermatology (1998), 138: 456-460.
Mrowietz et al., Treatment of psoriasis with fumaric acid esters (Fumaderm®), JDDG (2007), DOI: 10.1111/j.1610-0387.2007.06346.x, 2 pages.
Muller et al., "High-performance liquid chromatography/fluorescence detection of S-methylglutathione formed by glutathione-S-transferase T1 in vitro," Arch Toxicol, 2001, vol. 74, pp. 760-767.
Murakami et al., Suppression of a dextran sodium sulfate-induced colitis in mice by zerumbone, a subtropical ginger sesquiterpene, and nimesulide: separately and in combination. Biochemical Pharmacol (2003), 66, 1253-1261.
Naldi et al., Psoriasis (chronic plaque), Clin. Evid. (2009), 1(1706): 50 pages.
Nelson, et al., Effect of Dietary Inducer Dimethylfumarate on Glutathione in Cultured Human Retinal Pigment Epithelial Cells. Investigative Ophthalmology and Visual Science (1999), 40(9): 1927-1935.

(56) References Cited

OTHER PUBLICATIONS

Neymotin et al., Neuroprotective effect of Nrf2/AFE activators, CDDO ethylamide and CDDO trifluoroethylamide, in a mouse model of amyotrophic lateral sclerosis, Free Rad. Bio. Med (2011), 51: 88-96.
Nibbering et al., Intracellular signalling by binding sites for the antipsoriatic agent monomethylfumarate on human granulocytes, Br. J. Dermatol. (1997), 137: 65-75.
Offermans, The nicotinic acid receptor GPR109A (HM74A or PUMA-G) as a new therapeutic agent, Trends Pharm. Sci. (2006), 27(7): 384-390.
O'Toole, et al., Treatment of Carcinoid Syndrome: A Prospective Crossover Evaluation of Lanreotide versus Octreotide in Terms of Efficacy, Patient Acceptability, and Tolerance, American Cancer Society, Feb. 15, 2000, 88(4), 770-776.
Panagiotou et al., "Form Nanoparticles via Controlled Crystallization," Chemical Engineering Progress; Oct. 2008, 104, 10, pp. 33-39.
Pathak et al., "Supercritical fluid technology for enhanced drug delivery," Expert Opin. Drug Deliv. (2005) 2(4):747-761.
Peeters et al., Fumaric acid therapy for psoriatic arthritis. A randomized, double-blind, placebo-controlled study, Br. J. Rheumatol. (1992), 31(7): 502-504.
Pemble et al., "Human glutathione S-transferase Theta (GSTT1): cDNA cloning and the characterization of a genetic polymorphism," Biochem. J., 1994, vol. 300, pp. 271-276.
Rantanen, the cause of the Chinese sofa/chair dermatitis epidemic is likely to be contact allergy to dimethylfumarate, a novel potent contact sensitizer, Br. J. Dermatol. (2008), 159: 218-221.
Reddingius, Bioanalysis and pharmacokinetics of fumarates in humans, Ph.D. dissertation ETH No. 12199, Swiss Fed. Inst. Tech. Zurich (1997), 82 pages.
Reich et al., Efficacy and safety of fumaric acid esters in the long-term treatment of psoriasis—a retrospective study (FUTURE), JDDG (2009), DOI: 10.1111/j.1610-0387.2009.07120.x, 8 pages.
Richman et al., Nicotinic acid receptor agonists differentially activate downstream effectors, J. Bio. Chem. (2007), 282(25): 18028-18036.
Roll et al., Use of fumaric acid esters in psoriasis, Indian J. Dermatol. Ven. Lep. (2007), 73: 133-137.
Rostami-Yazdi, et al., "Detection of Metabolites of Fumaric Acid Esters in Human Urine: Implications for their mode of action", Journal of Investigative Dermatology, 2008, pp. 1-3.
Rostami-Yazdi et al., Pharmacokinetics of antipsoriatic fumaric acid esters in psoriasis patients, Arch. Dermatol. Res. (2010), 302: 531-538.
Rubant et al., Dimethylfumarate reduces leukocyte rolling in vivo through modulation of adhesion molecule expression, J. Invest. Dermatol. (2007), 128: 326-331.
Sawant et al., "Necessity of Establishing Chemical Integrity of Polymorphs of Drug Substance Using a Combination of NMR, HPLC, Elemental Analysis, and Solid-State Characterization Techniques: Case Studies," Organic Process Research & Development (2013), vol. 17, No. 3, pp. 519-532.
Schafer et al., "Failure is an option: learning from unsuccessful proof-of-concept trials", Drug Discovery Today, vol. 13, Nos. 21/22; Nov. 2008; pp. 913-916.
Schmidt, et al., "Reactivity of dimethyl fumarate and methylhydrogen fumarate towards glutathione and N-acetyl-1-cysteine-Preparation of S-substituted thiosuccinic acid esters", Bioorganic & Medicinal Chemistry, Pergamon, GB, vol. 15, No. 1 Nov. 15, 2006, pp. 333-342.
Seder et al., Acquisition of lymphokine-producing phenotype by CD4+ T-cells, Ann. Rev. Immunol. (1994), 12: 635-73.
Shan et al., "The role of cocrystals in pharmaceutical science," Drug Discovery Today (2008), 13(9/10), pp. 440-446.
Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, Ind. J. Chem. (2004) 43B: 1758-1764.
Soelberg Sorensen et al., Oral fumarate for relapsing-remitting multiple sclerosis, Lancet (2008), 372: 1447-1448.

Spencer et al., Induction of glutathione transferases and NAD(P)H: quinone reductase by fumaric acid derivatives in rodent cells and tissues, Cancer Res. (1990), 50: 7871-7875.
Spencer, "Tecfidera: an approach for repurposing," Pharmaceutical Patent Analyst, 2014, vol. 3(2), pp. 183-198.
Sprenger et al., "Characterization of the glutathione S-transferase GSTT1 deletion: discrimination of all genotypes by polymerase chain reaction indicates a trimodular genotype-phenotype correlation," Pharmacogenetics, 2000, vol. 10, pp. 557-565.
Stoof et al., The antipsoriatic drug dimethylfumarate strongly suppresses chemokine production in human keratinocytes and peripheral blood mononuclear cells, Br. J. Dermatol. (2001), 144: 1114-1120.
Talath et al., Stability studies of some glycolamide ester prodrugs of niflumic acid in aqueous buffers and human plasma by HPLC with UV detection, Arz. Forsch Drug Res. (2006), 56(9): 631-639.
Talath et al., Synthesis, stability studies, anti-inflammatory activity and ulcerogenicity of morpholinoalkyl ester prodrugs of niflumic acid, Arz. Forsch Drug Res. (2006), 56(11): 744-752.
Tang et al., The psoriasis drug monomethylfumarate is a potent nicotinic acid receptor agonist, Biochem. Biophys. Res. Comm. (2008), doi:10.1016/j.bbrc.2008.08.041, 4 pages.
Thing et al., "Prolonged naproxen joint residence time after intra-articular injection of lipophilic solutions comprising a naproxen glycolamide ester prodrug in the rat", International Journal of Pharmaceutics 451; Apr. 2013; pp. 34-40.
Thomson et al., FK 506: a novel immunosuppressant for treatment of autoimmune disease: rationale and preliminary clinical experience at the University of Pittsburgh, Springer Semin. Immunopathol. (1993), 14(4): 323-344.
Van Schoor et al., Effect of inhaled fluticasone on bronchial responsiveness to neurokinin A in asthma. Eur Respir J (2002), 19, 997-1002.
Van Schoor et al., The effect of the NK2 tachykinin receptor antagonist SR 48968 (saredutant) on neurokinin A-induced bronchoconstriction in asthmatics, Eur Respir J (1998) 12: 17-23.
Villegas et al., A new flavonoid derivative, dosmalfate, attenuates the development of dextran sulphate sodium-induced colitis in mice. Int'l Immunopharmacol (2003), 3, 1731-1741.
Vishweshwar et al., "Pharmaceutical Co-Crystals," Journal of Pharmaceutical Sciences (2006), 95(3), pp. 499-516.
Wadhwa et al., Glycolamide esters of 6-methoxy-2-naphthylacetic acid as potential prodrugs—Synthetic and spectral studies, Ind. J. Chem. (1995), 34B: 408-415.
Wain et al., Treatment of severe, recalcitrant, chronic plaque psoriasis with fumaric acid esters: a prospective study, Br. J. Dermatol. (2009), DOI 10.1111/j.1365-2133.2009.09267.x, 8 pages.
Wang, et al., Evidence-Based Treatment of Chronic Leg Ulcers in a Patient with Necrobiosis Lipoidica Deabeticorum. Chinese Journal of Evidence-Based Medicine (2007), 7(11): 830-835.
Weber et al., Synthesis, In Vitro Skin Permeation Studies, and PLS-Analysis of New Naproxen Derivatives, Pharm. Res. (2001) 18(5): 600-607.
Weber et al., Treatment of disseminated granuloma annulare with low-dose fumaric acid, Acta Derm. Venereol. (2009), 89: 295-298.
Werdenberg et al., Presystemic metabolism and intestinal absorption of antipsoriatic fumaric acid esters, Biopharm. Drug. Dispos. (2003), 24: 259-273.
Whiteley et al., Models of Inflammation: Measuring Gastrointestinal Ulceration in the Rat, Curr. Protocol. Pharm. (1998): 10.2.1-10.2.4.
Winkler, et al., Oxidative damage and age-related macular degeneration. Molecular vision, (1999), 5:32, 11 pages.
Woodworth et al., Oral BG-12 in combination with interferon beta or glatiramer acetate: pharmacokinetics, safety and tolerability, 26th Congress Eur. Cmtee. Treat. Res. Mult. Soler. (2010), poster: 1 page.
Woodworth et al., "Pharmacokinetics of Oral BG-12 Alone Compared with BG-12 and Interferon B-1a or Glatiramer Acetate Administered Together, Studied in Healthy Volunteers", Poster P04.207 presented at the 62nd Annual Meeting of the American Academy of Neurology, Apr. 10-17, 2010, Toronto, Ontario, Canada, 2 pages.
Wu et al., "Regulatory perspectives of Type II prodrug development and time-dependent toxicity management: Nonclinical Pharm/Tox analysis and the role of comparative toxicology", Science Direct, Toxicology 236; Apr. 2007; pp. 1-6.

(56) References Cited

OTHER PUBLICATIONS

Wustrow et al., Comparison of the efficacy and tolerability of a novel methyl hydrogenfumarate prodrug with dimethylfumarate in rodent EAE and GI irritation models, XenoPort, Inc., Oct. 13-16, 2010, 1 page.

Xenoport, Inc., XenoPort announces presentation of preclinical data for novel fumarate analog XP23829 at ECTRIMS, Press Release dated Oct. 13, 2010, 3 pages.

Yamada et al., "Synthesis and Polymerization of Unsaturated Dibasic Acid Derivatives," Yuki Gosei Kagaku Kyokaishi (1965), 23(2), 19 pages.

Yang et al., Neuroprotective effects of the triterpenoid, CDDO methyl amide, a potent inducer of Nrf2-mediated transcription, PLOS One (2009), 4(6) doi:10.1371/journal.pone.0005757: 13 pages.

Zhu et al., Inhibition of dendritic cell differentiation by fumaric acid esters, J. Invest. Dermatol. (2001), 116: 203-208.

Steckel et al., "The extrusion and speronization of chitosan," Pharmaceutical Technology Europe, <http://www.pharmtech.com/extrusion-and-spheronization-chitosan>, published Jul. 2, 2007, pp. 1-12.

Mannervik et al., "Identification of three classes of cytosolic glutathione transferase common to several mammalian species: Correlation between structural data and enzymatic properties," Proc. Natl. Acad. Sci., USA, Nov. 1985, vol. 82, pp. 7202-7206.

Atreya, "NF-kB in inflammatory bowel disease," Symposium, Journal of Internal Medicine, 2008, 263(6), pp. 591-596.

Barnes, "Mediators of Chronic Obstructive Pulmonary Disease," Pharmacological Reviews, 2004, 56(4), pp. 515-548.

Blandini et al., "Glutamate and Parkinson's Disease," Molecular Neurobiology, 1996, vol. 12, pp. 73-94.

Brewer et al., "Fumaric acid esters in the management of severe psoriasis," Clinical and Expreriemental Dermatology, 2007, vol. 32, pp. 246-249.

Camandola et al., "NF-kB as a therapeutic target in neurodegenerative diseases," Expert Opinion Ther. Targets, 2007, 11(2) pp. 123-132.

D'Acquisito et al., "Inhibition of Nuclear Factor Kappa B (NF-kB): An Emerging Theme in Anti-Inflammatory Therapies," Molecular Interventions, 2002, 2(1), pp. 22-35.

Dawson et al., "Bioequivalence of BG-12 (Dimethyl Fumarate) Administered as a Single 240 mg Capsule and Two 120 mg Capsules: Findings from a Randomized, Two-period Crossover Study," Poster P913, 28th Congress of the European Committee for Treatment and Research in Multiple Sclerosis, 2012, Lyon, France, 1 page.

Dymicky, "Preparation of Monomethyl Fumarate," Organic Preparations and Procedures International, 1983, 15(4), pp. 233-238.

Gesser et al., "Dimethylfumarate Specifically Inhibits the Mitogen and Stress-Activated Kinases 1 and 2 (MSK1/2): Possible Role for its Anti-Psoriatic Effect," Journal of Investigative Dermatology, 2007, vol. 127, pp. 2129-2137.

Hoefnagel, "Long-term safety aspects of systemic therapy with fumaric acid esters in severe psoriasis," British Journal of Dermatology, 2003, vol. 149, pp. 363-369.

Lehmann et al., "Fumaric acid esters are potent immunosuppressants: inhibition of acute and chronic rejection in rat kidney transplantation models by methyl hydrogen fumarate," Arch. Dermatol. Res., 2002, vol. 294, pp. 399-404.

Lehmann et al., "Dimethylfumarate Induces Immunosuppression via Glutathione Depletion and Subsequent Induction of Heme Oxygenase 1," Journal of Investigative Dermatology, 2007, vol. 127, pp. 835-845.

Loewe et al., "Dimethylfumarate Inhibits TNF-Induced Nuclear Entry of NF-kB/p65 in Human Endothelial Cells," The Journal of Immunology, 2002, vol. 168, pp. 4781-4787.

Martin, "Molecular Basis of the Neurodegenerative Disorders," The New England Journal of Medicine, 1999, vol. 344, pp. 1970-1980.

Mrowietz et al., "Dimethylfumarate for psoriasis: more than a dietary curiosity," Trends in Molecular Medicine, 2005, 11(1), pp. 43-48.

Mrowietz et al., "Treatment of severe psoriasis with fumaric acid esters: scientific background and guidelines for therapeutic use," British Journal of Dermatology, 1999, vol. 141, pp. 424-429.

Nielsen et al., "Glycolamide Esters as Biolabile Prodrugs of Carboxylic Acid Agents: Synthesis, Stability, Bioconversion, and Physicochemical Properties," Journal of Pharmaceutical Sciences, 1988, 77(4), pp. 285-298.

Rowland et al., "Amyotrophic Lateral Sclerosis," The New England Journal of Medicine, 2001, 344(22), pp. 1688-1700.

Schilling et al., "Fumaric acid esters are effective in chronic experimental autoimmune encephalomyelitis and suppress macrophage infiltration," Clinical and Experimental Immunology, 2006, vol. 145, pp. 101-107.

Schimrigk et al., "Oral fumaric acid esters for the treatment of active multiple sclerosis: an open-label, baseline-controlled pilot study," European Journal of Neurology, 2006, vol. 13, pp. 604-610.

Sheikh et al., "Safety, Tolerability, and Pharmacokinetics of BG-12 Administered with and without Aspirin: Key Findings from a Randomized, Double-Blind, Placebo-Controlled Trial in Healthy Volunteers," Poster P04.136, 64th Annual Meeting of the American Academy of Neurology, 2012, New Orleans, LA, 1 page.

Spatz et al., "Methyl Hydrogen Fumarate," Journal of Organic Chemistry, 1958, vol. 23, pp. 1559-1560.

Tabruyn et al., "NF-kB: a new player in angiostatic therapy," Angiogenesis, 2008, vol. 11, pp. 101-106.

Tracey et al., "Tumor necrosis factor antagonist mechanisms of action: A comprehensive review," Pharmacology & Therapeutics, 2008, vol. 117, pp. 244-279.

Treumer et al., "Dimethylfumarate Is a Potent Inducer of Apoptosis in Human T Cells," The Journal of Investigative Dermatology, 2003, vol. 121, pp. 1383-1388.

Vandermeeren et al., "Dimethylfumarate Is an Inhibitor of Cytokine-Induced E-Selectin, VCAM-1, and ICAM-1 Expression in Human Endothelial Cells," Biochemical and Biophysical Research Communications, 1997, vol. 234, pp. 19-23.

Virley, "Developing Therapeutics for the Treatment of Multiple Sclerosis," The Journal of the American Society for Experimental NeuroTherapeutics, 2005, 2(4), pp. 638-349.

Wakkee et al., "Drug evaluation: BG-12, an immunomodulatory dimethylfumarate," Current Opinion in Investigational Drugs, 2007, 8(11), pp. 955-962.

Wingerchuk et al., "Multiple Sclerosis: Current Pathophysiological Concepts," Laboratory Investigation, 2001, 81 (3), pp. 263-281.

Woodworth et al., "Pharmacokinetics of Oral BG-12 Alone Compared with BG-12 and Interferon Beta-1a or Glatiramer Acetate Administered Together, Studied in Healthy Volunteers," Poster P04.207, 62nd Annual Meeting of the American Academy of Neurology, 2010, Toronto, Ontario, Canada, 1 page.

Yazdi et al., "Fumaric acid esters," Clinics in Dermatology, 2008, vol. 26, pp. 522-526.

Lei et al., "Novel Technology of Dimethyl Fumarate Synthesis," Ziyuan Kaifa Yu Shichang (2011), 27(9), pp. 787-789.

Zhao et al., "Synthesis and antimicrobial active of monomethyl fumarate," Shipin Gongye Keji (2008), 29(6), pp. 259-262.

Zhang et al., "Synthesis of Dimethyl Fumarate with Orthogonal Test," Jingxi Huagong Zhongjianti (2006), 36(6), pp. 71-72.

Zheng et al., "Improved Preparation of Monomethyl Fumarate," Huaxue Shijie (2004), 45(4), pp. 207-208, 217.

O'Donnell et al., "Remington The Science and Practice of Pharmacy" 21st Edition, 2005, Chapter 52, pp. 1025-1036.

Bhattacharya et al., Polymorphism in Pharmaceutical Solids: Thermoanalytical and Crystallographic Methods 334 (Brittain H. ed., 2d ed. Informa Healthcare USA, Inc. 2009) (1999), 20 pp.

Ivanisevic et al., "Uses of X-Ray Powder Diffraction in the Pharmaceutical Industry," Pharmaceutical Formulation & Quality, 32 (2011), pp. 30-33.

\* cited by examiner

METHOD OF MAKING MONOMETHYL FUMARATE

CROSS-REFERENCE

This application claims the benefit under 35 U.S.C. §119 (e) of U.S. Provisional Application Ser. No. 61/832,665, filed Jun. 7, 2013, and entitled "Method of Making Monomethyl Fumarate," which is incorporated by reference in its entirety.

FIELD

Disclosed herein are methods of making monomethyl fumarate, which can then also be used in methods of making prodrugs of monomethyl fumarate. Both monomethyl fumarate and prodrugs of monomethyl fumarate are useful for treating neurodegenerative, inflammatory, and autoimmune diseases including multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

BACKGROUND

Fumaric acid esters (FAEs) such as dimethyl fumarate are approved in Germany for the treatment of psoriasis, are approved in the United States for the treatment of multiple sclerosis, are being evaluated in the United States for the treatment of psoriasis, and have been proposed for use in treating a wide range of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, Trends Mol Med 2005, 111 (1), 43-48; and Yazdi and Mrowietz, Clinics Dermatology 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al., Arch Dermatol Res 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); advanced glycation end products (AGE)-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

The mechanism of action of fumaric acid esters is believed to be mediated by pathways associated with the immunological response. For example, FAEs invoke a shift from a Th1 to Th2 immune response, favorably altering the cytokine profile; inhibit cytokine-induced expression of adhesion molecules such as VCAM-1, ICAM-1 and E-selectin, thereby reducing immune cell extravasation; and deplete lymphocytes through apoptotic mechanisms (Lehmann et al., J Investigative Dermatology 2007, 127, 835-845; Gesser et al., J Investigative Dermatology 2007, 127, 2129-2137; Vandermeeren et al., Biochm Biophys Res Commun 1997, 234, 19-23; and Treumer et al., J Invest Dermatol 2003, 121, 1383-1388).

Recent studies suggest that FAEs are inhibitors of NF-κB activation, a transcription factor that regulates the inducible expression of proinflammatory mediators (D'Acquisto et al., Molecular Interventions 2002, 2 (1), 22-35). Accordingly, FAEs have been proposed for use in treating NF-κB mediated diseases (Joshi et al., WO 2002/055066; and Joshi and Strebel, WO 2002/055063, US 2006/0205659, U.S. Pat. No. 7,157,423 and U.S. Pat. No. 6,509,376). Inhibitors of NF-κB activation have also been shown to be useful in angiostatic therapy (Tabruyn and Griffioen, Angiogenesis 2008, 11, 101-106), inflammatory bowel disease (Atreya et al., J Intern Med 2008, 263 (6), 591-6); and in animal models of diseases involving inflammation including neutrophilic alveolitis, asthma, hepatitis, inflammatory bowel disease, neurodegeneration, ischemia/reperfusion, septic shock, glomerulonephritis, and rheumatoid arthritis (D'Acquisto et al., Molecular Interventions 2002, 2 (1), 22-35).

Studies also suggest that NF-κB inhibition by FAEs may be mediated by interaction with tumor necrosis factor (TNF) signaling. Dimethyl fumarate inhibits TNF-induced tissue factor mRNA and protein expression and TNF-induced DNA binding of NF-κB proteins, and inhibits the TNF-induced nuclear entry of activated NF-κB proteins thereby inhibiting inflammatory gene activation (Loewe et al., J Immunology 2002, 168, 4781-4787). TNF signaling pathways are implicated in the pathogenesis of immune-mediated inflammatory diseases such as rheumatoid arthritis, Crohn's disease, psoriasis, psoriatic arthritis, juvenile idiopathic arthritis, and ankylosing spondylitis (Tracey et al., Pharmacology & Therapetuics 2008, 117, 244-279).

FUMADERM®, an enteric coated tablet containing a salt mixture of ethyl hydrogen fumarate and dimethyl fumarate (DMF) (2), which is rapidly hydrolyzed to methyl hydrogen fumarate (MHF) (1) in vivo and is regarded as the main bioactive metabolite, was approved in Germany in 1994 for the treatment of psoriasis.

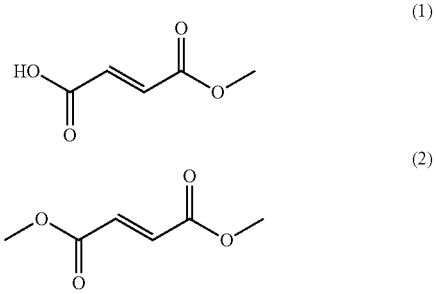

FUMADERM® is dosed three times/day with 1-2 grams/day administered for the treatment of psoriasis. FUMADERM® exhibits a high degree of interpatient variability with respect to drug absorption and food strongly reduces bioavailability. Absorption is thought to occur in the small intestine with peak levels achieved 5-6 hours after oral administration.

Significant side effects occur in 70-90% of patients (Brewer and Rogers, *Clin Expt'l Dermatology* 2007, 32, 246-49; and Hoefnagel et al., *Br J Dermatology* 2003, 149, 363-369). Side effects of current FAEs therapy include gastrointestinal upset including nausea, vomiting, diarrhea, and transient flushing of the skin. Also, DMF exhibits poor aqueous solubility.

Tecfidera™, formerly called BG-12, is a delayed release (i.e., a capsule containing enteric-coated microtablets) oral dosage form of dimethyl fumarate. Tecfidera™ (dimethyl fumarate) was approved in the USA in 2013, and is dosed two times per day with 480 mgs/day administered for the treatment of multiple sclerosis. Details concerning the clinical testing of BG-12 are disclosed in Sheikh et al., Safety Tolerability and Pharmacokinetics of BG-12 Administered with and without Aspirin, Key Findings from a Randomized, Double-blind, Placebo-controlled Trial in Healthy Volunteers, Poster PO4.136 presented at the 64$^{th}$ Annual Meeting of the American Academy of Neurology, Apr. 21-28, 2012, New Orleans, La.; Dawson et al., Bioequivalence of BG-12 (Dimethyl Fumarate) Administered as a Single 240 mg Capsule and Two 120 mg Capsules: Findings from a Randomized, Two-period Crossover Study, Poster P913 presented at the 28th Congress of the European Committee for Treatment and Research in Multiple Sclerosis, Oct. 10-13, 2012, Lyon, France; and Woodworth et al., Pharmacokinetics of Oral BG-12 Alone Compared with BG-12 and Interferon β-1a or Glatiramer Acetate Administered Together, Studied in Health Volunteers, Poster PO4.207 presented at the 62$^{nd}$ Annual Meeting of the American Academy of Neurology, Apr. 10-17, 2010, Toronto, Ontario, Canada.

Fumaric acid derivatives (Joshi and Strebel, WO 2002/055063, US 2006/0205659, and U.S. Pat. No. 7,157,423 (amide compounds and protein-fumarate conjugates); Joshi et al., WO 2002/055066 and Joshi and Strebel, U.S. Pat. No. 6,355,676 (mono and dialkyl esters); Joshi and Strebel, WO 2003/087174 (carbocyclic and oxacarbocyclic compounds); Joshi et al., WO 2006/122652 (thiosuccinates); Joshi et al., US 2008/0233185 (dialkyl and diaryl esters)) and salts (Nilsson et al., US 2008/0004344) have been developed in an effort to overcome the deficiencies of current FAEs therapy. Controlled release pharmaceutical compositions comprising fumaric acid esters are disclosed by Nilsson and Müller, WO 2007/042034. Glycolamide ester prodrugs are described by Nielsen and Bundgaard, *J Pharm Sci* 1988, 77 (4), 285-298.

Gangakhedkar et al., U.S. Patent Publication No. 2010/0048651, discloses prodrugs of monomethyl fumarate having the following chemical formula:

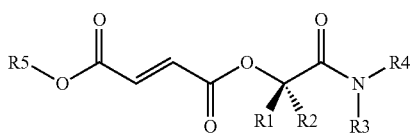

wherein:
$R^1$ and $R^2$ are independently chosen from hydrogen, $C_{1-6}$ alkyl, and substituted $C_{1-6}$ alkyl;
$R^3$ and $R^4$, together with the nitrogen to which they are bonded, can form a $C_{5-10}$-heteroaryl ring such as a morpholino ring; and $R^5$ can be hydrogen, methyl, ethyl, and $C_{3-6}$ alkyl; and pharmaceutical compositions containing such compounds for the treatment of diseases including psoriasis, multiple sclerosis, an inflammatory bowel disease, asthma, chronic obstructive pulmonary disease, Parkinson's disease, Huntington's disease, amyotrophic lateral sclerosis (ALS), and arthritis. When $R^5$ is methyl, such compounds are prodrugs of monomethyl fumarate. These glycol amide prodrugs of monomethyl fumarate can be prepared by reacting monomethyl fumarate with a reactant comprising the glycol amide promoiety. In general, the starting monomethyl fumarate can be prepared by isomerization of the corresponding monomethyl maleate.

For example, Guzowski et al., WO2012/170923, discloses preparation of monomethyl fumarate by esterification of fumaric acid with methanol in the presence of sulfuric acid.

Lei et al., Ziyuan Kaifa Yu Shichang (2011), 27 (9), 787-789, discloses preparation of monomethyl fumarate via isomerization of monomethyl maleate using hydrochloric acid.

Zhao et al., Shipin Gongye Keji (2008), 29 (6), 259-262, discloses preparation of monomethyl fumarate via isomerization of monomethyl maleate using 2 wt % hydrochloric acid as a catalyst.

Zhang et al., Jingxi Huagong Zhongjianti (2006), 36 (6), 71-72, discloses preparation of monomethyl fumarate via isomerization of monomethyl maleate using phosphoric acid as a catalyst.

Zheng et al., Huaxue Shijie (2004), 45 (4), 207-208, 217, discloses preparation of monomethyl fumarate via isomerization of monomethyl maleate using phosphoric acid and $AlCl_3$ as a catalyst.

Gu et al., Faming Zhuanli Shenqing (2010), CN 101774913, discloses preparation of monomethyl fumarate via isomerization of monomethyl maleate using fumaryl chloride as a catalyst.

Li et al., Faming Zhuanli Shenqing Gongkai Shuomingshu (2005), CN 1616400, discloses preparation of monomethyl fumarate via isomerization of monomethyl maleate using hydrogen halide as a catalyst.

Takaoka et al., Jpn. Kokai Tokkyo Koho (1991), JP 03294245, discloses preparation of monomethyl fumarate via isomerization of monomethyl maleate in the presence of aq. NaBr and aq. $K_2S_2O_8$.

Ikebe et al., Jpn. Kokai Tokkyo Koho (1985), JP 60181047, discloses preparation of monomethyl fumarate via isomerization of monomethyl maleate in the presence of quaternary ammonium bromide and organic peroxide.

Dyicky, Organic Preparations and Procedure International (1983), 15 (4), 233-8, discloses preparation of monomethyl fumarate via isomerization of monomethyl maleate using HCl, $AlCl_3$, or phthaloyl chloride as a catalyst.

Schweckendiek et al., German Patent (1964) DE 1165586, discloses preparation of monomethyl fumarate via isomerization of monomethyl maleate using oxalyl chloride as a catalyst.

Spatz, et al., Journal of Organic Chemistry (1958), 23, 1559-60, discloses preparation of monomethyl fumarate via isomerization of monomethyl maleate using thiourea as a catalyst.

SUMMARY

To prepare prodrugs of monomethyl fumarate (MMF) for human pharmaceutical use, it is desirable to start with relatively pure MMF. While aforementioned methods for preparation of MMF are known in the literature, these methods result in MMF contaminated with various impurities. Many of the undesired impurities are formed due to the use of water in reactions and/or during the aqueous work-up. In particular, monomethyl sulfate and dimethyl sulfates are byproducts when sulfuric acid is used as catalyst. Dimethyl sulfate has been shown to be genotoxic as an impurity.

Therefore, there is a need for alternate efficient methods for preparation of highly pure MMF, particularly for manufacturing scale production of MMF. The methods described herein are directed toward this end.

In one aspect, the present disclosure provides processes for preparing monomethyl fumarate (MMF).

In another aspect, the present disclosure provides processes for preparing prodrugs of monomethyl fumarate.

In yet another aspect, the present disclosure provides processes for preparing monomethyl fumarate (MMF) or a prodrug thereof; comprising reacting monomethyl maleate with a compound of formula (II)

to produce MMF;
wherein $R^1$ is selected from unsubstituted $C_1$-$C_6$ alkyl, unsubstituted $C_3$-$C_6$ cycloalkyl, substituted $C_1$-$C_6$ alkyl and substituted $C_3$-$C_6$ cycloalkyl; and the substitution is selected from halo and $C_1$-$C_6$ alkoxy.

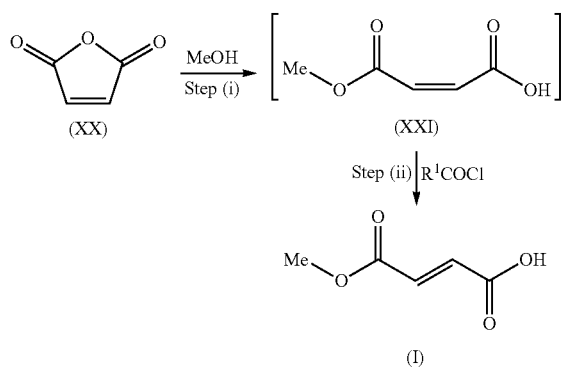

In a particular embodiment, with respect to the process, $R^1$ is Me. Multiple advantages have been demonstrated for the process disclosed herein, including (i) avoiding the use of water or other aqueous media, thereby minimizing formation of undesired side-products or impurities from hydrolysis; (ii) generating volatile byproducts which can be easily removed during product isolation (for example by distillation); (iii) producing the desired product MMF in high yield; and (iv) producing MMF in very high purity, thereby avoiding the need for further purification. No toxic impurities were formed.

Other objects and advantages will become apparent to those skilled in the art from a consideration of the ensuing detailed description. Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification and the drawings, which forms a part of this disclosure.

DETAILED DESCRIPTION

Definitions

The present disclosure may be understood by reference to the following detailed description. It is noted that, for purposes of illustrative clarity, certain elements in various drawings may not be drawn to scale, may be represented schematically or conceptually, or otherwise may not correspond exactly to certain physical configurations of embodiments.

"Alkyl" refers to a radical of a straight-chain or branched saturated hydrocarbon group having from 1 to 20 carbon atoms ("$C_{1-20}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Leaving group" has the meaning conventionally associated with it in synthetic organic chemistry, i.e., an atom or a group capable of being displaced by a nucleophile and includes halogen such as chloro, bromo, fluoro, and iodo; acyloxy, such as acetoxy and benzoyloxy, alkoxycarbonylaryloxycarbonyl, mesyloxy, tosyloxy, and trifluoromethanesulfonyloxy; aryloxy such as 2,4-dinitrophenoxy, methoxy, N,O-dimethylhydroxylamino, p-nitrophenolate, imidazolyl, and the like.

"Monomethyl fumarate" refers to the monomethyl ester of fumaric acid. The compound has the following chemical structure:

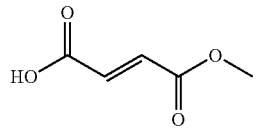

and has a molecular weight of 130.10 daltons. The compound is also commonly referred to as 2(E)-Butenedioic acid 1-methyl ester, (2E)-4-Methoxy-4-oxobut-2-enoic acid; Fumaric acid hydrogen 1-methyl ester; (2E)-2-Butenedioic acid 1-methyl ester; (E)-2-Butenedioic acid monomethyl ester; Monomethyl trans-ethylene-1,2-dicarboxylate; and methyl hydrogen fumarate. The compound is also referred to herein and elsewhere by the acronyms MMF and/or MHF.

OTHER DEFINITIONS

"One-pot process" refers to a chemical process in which the chemical reaction(s) occur in a single reactor, thereby avoiding a separation process and/or purification of any intermediate chemical compounds, e.g., between successive chemical reactions.

"Prodrug of monomethyl fumarate" refers to a derivative of monomethyl fumarate that requires a chemical transformation within a patient's body to convert the prodrug into the active monomethyl fumarate metabolite. Prodrugs of monomethyl fumarate can be, although are not necessarily, pharmacologically inactive until converted to the active monomethyl fumarate. Similarly, the term "promoiety" refers to a form of protecting group that when used to mask a functional group (e.g., carboxylic acid moiety) within the monomethyl fumarate molecule converts the monomethyl fumarate into a monomethyl fumarate prodrug. For example, the promoiety may be attached to the monomethyl fumarate molecule via (e.g., ester or amide) bond(s) that are cleaved by enzymatic or non-enzymatic means in vivo.

Methods

In one aspect, the present disclosure provides processes for preparing monomethyl fumarate (MMF). The process disclosed herein avoids the use of aqueous media or water, in the reactions as well as in the reaction work-ups, thereby minimizing formation of any undesired side-products from hydrolysis. Additionally, the reactions of the process form volatile byproducts, thus they can be easily separated or removed by simple distillation under reduced pressure. Furthermore, the process of the present disclosure produces the desired MMF product in high yield and substantially free from potentially toxic impurities, such as dimethyl sulfate. Moreover, and more importantly, the process produces MMF in very high purity, thereby avoiding any need for further purification.

In another aspect, the present disclosure provides the use of monomethyl fumarate for preparing prodrugs of monomethyl fumarate.

In yet another aspect, the present disclosure provides processes for preparing monomethyl fumarate (MMF) (I):

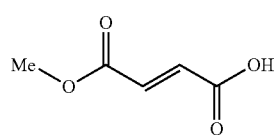

or a prodrug thereof; comprising reacting monomethyl maleate with a compound of formula (II)

to produce MMF; wherein $R^1$ is selected from substituted or unsubstituted $C_1$-$C_6$ alkyl and substituted or unsubstituted $C_3$-$C_6$ cycloalkyl.

In one embodiment, $R^1$ is unsubstituted $C_1$-$C_6$ alkyl or unsubstituted $C_3$-$C_6$ cycloalkyl.

In one embodiment, $R^1$ is substituted $C_1$-$C_6$ alkyl or substituted $C_3$-$C_6$ cycloalkyl; and the substitution is selected from halo and $C_1$-$C_6$ alkoxy.

In one embodiment, $R^1$ is selected from Me, Et, n-Pr, i-Pr, n-Bu, i-Bu, sec-Bu, t-Bu, n-pentyl, n-hexyl, cyclopropyl, cyclobutyl, cyclopentyl, and cyclohexyl. In another embodiment, $R^1$ is selected from Me, Et, n-Pr, i-Pr, and cyclopropyl. In a particular embodiment, $R^1$ is selected from Me and cyclopropyl. In a more particular embodiment, $R^1$ is Me.

In one embodiment, the compound of formula (II) is $R^1$C(O)Cl.

In one embodiment, $R^1$C(O)Cl is MeC(O)Cl, EtC(O)Cl, n-Pr—C(O)Cl, i-Pr—C(O)Cl, n-Bu-C(O)Cl, i-Bu-C(O)Cl, sec-Bu-C(O)Cl, or t-Bu-C(O)Cl.

In one embodiment, $R^1$C(O)Cl is acetyl chloride, propanoyl chloride, butanoyl chloride, pentanoyl chloride, or pivaloyl chloride.

In a particular embodiment, $R^1$C(O)Cl is MeC(O)Cl or acetyl chloride.

In one embodiment, with respect to the reaction of monomethyl maleate with the compound of formula (II), the reaction occurs in a solvent. In one embodiment, the solvent is selected from the group consisting of acetonitrile, benzonitrile, hexane, heptane, toluene, xylene, anisole, cumene, chlorobenzene, cyclohexane, methylcyclohexane, ethyl acetate, dichloromethane, dichloroethane, trichloroethane, tetrachloroethane, tetrahydrofuran, diphenyl ether, methyl tert-butyl ether, dioxane, dimethoxyethane, diethoxyethane, dibutyl ether, diisopropyl ether, and combinations thereof. In a particular embodiment, the solvent is selected from toluene and acetonitrile. In a more particular embodiment, the solvent is toluene.

In one embodiment, with respect to the reaction of monomethyl maleate with the compound of formula (II), the monomethyl maleate and solvent are present in amounts to provide a molar ratio of the monomethyl maleate to solvent in a range of about 1 to 50 to about 1 to 1. In another embodiment, the ratio of monomethyl maleate to solvent is in a range of about 1 to 50, about 1 to 25, about 1 to 20, about 1 to 15, about 1 to 10, about 1 to 8, about 1 to 5, about 1 to 4, about 1 to 3, about 1 to 2, or about 1 to 1. In a particular embodiment, the molar ratio is in a range of about 1 to 2.

In a particular embodiment, with respect to the reaction of monomethyl maleate with the compound of formula (II), the reaction occurs in toluene; and the molar ratio of the monomethyl maleate to toluene is about 1 to 3.

In a particular embodiment, with respect to the reaction of monomethyl maleate with the compound of formula (II), the reaction occurs in toluene; and the molar ratio of the monomethyl maleate to toluene is about 1 to 2.

In one embodiment, with respect to the reaction of monomethyl maleate with the compound of formula (II), the monomethyl maleate and $R^1$C(O)Cl are present in amounts to provide a molar ratio of the monomethyl maleate to $R^1$C(O)Cl in a range of about 1 to 0.010 to about 1 to 1. In another embodiment, the molar ratio is in a range of about 1 to 0.010, about 1 to 0.015, about 1 to 0.020, about 1 to 0.025, about 1 to 0.030, about 1 to 0.035, about 1 to 0.040, or about 1 to 0.045, about 1 to 0.050, about 1 to 0.055, about 1 to 0.060, about 1 to 0.065, about 1 to 0.070, or about 1 to 0.075, about 1 to 0.080, about 1 to 0.085, about 1 to 0.090, about 1 to 0.095, about 1 to 0.100, about 1 to 0.105, about 1 to 0.110, about 1 to 0.115, about 1 to 0.120, about 1 to 0.125, about 1 to 0.130, about 1 to 0.135, about 1 to 0.140, about 1 to 0.145, about 1 to 0.150, about 1 to 0.160, about 1 to 0.170, about 1 to 0.180, about 1 to 0.190, or about 1 to 0.200. In yet another embodiment, the molar ratio is in a range of about 1 to 0.250, about 1 to 0.300, about 1 to 0.350, about 1 to 0.400, about 1 to 0.450, about 1 to 0.500, about 1 to 0.550, about 1 to 0.600, about 1 to 0.650, about 1 to 0.700, about 1 to 0.750, about 1 to 0.800, about 1 to 0.850, about 1 to 0.900, about 1 to 0.950, or about 1 to 1. In a particular embodiment, the molar ratio is in a range of about 1 to 0.010. In a more particular embodiment, the molar ratio is in a range of about 1 to 0.10.

In one embodiment, with respect to the reaction of monomethyl maleate with the compound of formula (II), $R^1C(O)Cl$ is present in a amount of about 1 to 100 mole % of the monomethyl maleate. In another embodiment, $R^1C(O)Cl$ is present in a amount of about 1 to 80 mole %, about 1 to 70 mole %, about 1 to 60 mole %, about 1 to 50 mole %, about 1 to 40 mole %, about 1 to 30 mole %, about 1 to 20 mole %, about 1 to 15 mole %, about 1 to 10 mole %, about 1 to 5 mole %, or about 1 to 3 mole %, of the monomethyl maleate. In a particular embodiment, $R^1C(O)Cl$ is present in a amount of about 1 to 20 mole % of the monomethyl maleate. In another particular embodiment, $R^1C(O)Cl$ is present in a amount of about 1 to 15 mole % of the monomethyl maleate. In another particular embodiment, $R^1C(O)Cl$ is present in a amount of about 1 to 10 mole % of the monomethyl maleate. In another particular embodiment, $R^1C(O)Cl$ is present in a amount of about 1 to 5 mole % of the monomethyl maleate.

In one embodiment, with respect to the reaction of monomethyl maleate with the compound of formula (II), the reaction occurs at a temperature ranging from about 50° C. to about 100° C. In another embodiment, the reaction occurs at a temperature ranging from about 50° C. to about 100° C., 60° C. to about 100° C., 60° C. to about 90° C., 70° C. to about 90° C., 70° C. to about 85° C., or about 80° C. to about 85° C. In another embodiment, the reaction occurs at a temperature ranging from about 60° C. to about 90° C. In a particular embodiment, the reaction occurs at a temperature ranging from about 70° C. to about 90° C. In another particular embodiment, the reaction occurs at a temperature ranging from about 70° C. to about 85° C. In a more particular embodiment, the reaction occurs at a temperature ranging from about 80° C. to about 85° C. In a most particular embodiment, the reaction occurs at a temperature of about 85° C.

In one embodiment, with respect to the reaction of monomethyl maleate with the compound of formula (II), the reaction occurs over a period of about 2 to 140 hours. In another embodiment, the reaction occurs over a period of about 2 hours to 24 hours. In another embodiment, the reaction occurs over a period of about 2 hours to 20 hours. In another embodiment, the reaction occurs over a period of about 4 hours to 15 hours. In a particular embodiment, the reaction occurs over a period of about 10 hours to 16 hours. In a more particular embodiment, the reaction occurs over a period of about 14 hours.

In a particular embodiment, with respect to the reaction of monomethyl maleate with the compound of formula (II), the reaction occurs in toluene, the MMF and toluene are present in amounts to provide a molar ratio of the monomethyl maleate to the toluene of about 1 to 3; the compound of formula (II) is acetyl chloride; the reaction occurs (i) in the presence of about 10 mole % of acetyl chloride, (ii) for a period of about 14 hours, and (iii) at a temperature of about 85° C.

In a particular embodiment, with respect to the reaction of monomethyl maleate with the compound of formula (II), the reaction occurs in toluene, the MMF and toluene are present in amounts to provide a molar ratio of the monomethyl maleate to the toluene of about 1 to 2; the compound of formula (II) is acetyl chloride; the reaction occurs (i) in the presence of about 10 mole % of acetyl chloride, (ii) for a period of about 14 hours, and (iii) at a temperature of about 85° C.

In one embodiment, the monomethyl maleate is prepared by reacting maleic anhydride with methanol.

In one embodiment, with respect to the reaction of maleic anhydride with methanol, the reaction occurs in the absence of a solvent. In another embodiment, the reaction occurs in the presence of a solvent.

In one embodiment, with respect to the reaction of maleic anhydride with methanol, the reaction occurs in a solvent. In one embodiment, the solvent is selected from the group consisting of acetonitrile, benzonitrile, hexane, heptane, toluene, xylene, anisole, cumene, chlorobenzene, cyclohexane, methylcyclohexane, ethyl acetate, dichloromethane, dichloroethane, trichloroethane, tetrachloroethane, tetrahydrofuran, diphenyl ether, methyl tert-butyl ether, dioxane, dimethoxyethane, diethoxyethane, dibutyl ether, diisopropyl ether and combinations thereof.

In a particular embodiment, with respect to the reaction of maleic anhydride with methanol, the reaction occurs in a solvent; and the solvent is toluene. In another particular embodiment, the solvent is acetonitrile.

In one embodiment, with respect to the reaction of maleic anhydride with methanol, the reaction occurs in a solvent; and the maleic anhydride and solvent are present in amounts that provide a molar ratio of the maleic anhydride to solvent in the range of about 1 to 25 to about 1 to 0.1. In another embodiment, the ratio is in the range of about 1 to 1.2 to about 1 to 1.4.

In one embodiment, with respect to the reaction of maleic anhydride with methanol, the reaction occurs in a solvent; and the maleic anhydride and solvent are present in amounts that provide a molar ratio of the maleic anhydride to solvent in the range of about 1 to 25, about 1 to 20, about 1 to 15, about 1 to 10, about 1 to 8, about 1 to 5, about 1 to 4, about 1 to 3, about 1 to 2, about 1 to 1, about 1 to 0.9, about 1 to 0.8, about 1 to 0.7, about 1 to 0.6, about 1 to 0.5, about 1 to 0.4, about 1 to 0.3, about 1 to 0.2 or about 1 to 0.1, about 1 to 0.6 or about 1 to 0.5, about 1 to 0.4, about 1 to 0.3, about 1 to 0.2 or about 1 to 0.1. In a particular embodiment, the molar ratio of the maleic anhydride to solvent is in the range of about 1 to 1, about 1 to 0.95, about 1 to 0.90, about 1 to 0.85, about 1 to 0.80, about 1 to 0.75, or about 1 to 0.70. In a more particular embodiment, the molar ratio is around 1 to 0.80.

In a particular embodiment, with respect to the reaction of maleic anhydride with methanol, the reaction occurs in toluene, and the molar ratio of maleic anhydride to toluene is about 1 to 3.

In a particular embodiment, with respect to the reaction of maleic anhydride with methanol, the reaction occurs in toluene, and the molar ratio of maleic anhydride to toluene is about 1 to 0.80.

In one embodiment, with respect to the reaction of maleic anhydride with methanol, the reaction occurs in a solvent; and the maleic anhydride and solvent are present in amounts that provide a molar ratio of the maleic anhydride to solvent in the range of about 1 to 0.98, about 1 to 0.99, about 1 to 1, about 1 to 1.10, about 1 to 1.15, about 1 to 1.20, about 1 to 1.30, or about 1 to 1.40, or about 1 to 1.50, about 1 to 1.60, about 1 to 1.70, or about 1 to 1.80, about 1 to 1.90, about 1 to 2.00, about 1 to 2.10, about 1 to 2.20, about 1 to 2.30, about 1 to 2.40, about 1 to 2.50, about 1 to 2.60, about 1 to 2.70, about 1 to 2.80, about 1 to 2.90, or about 1 to 3.00.

In one embodiment, with respect to the reaction of maleic anhydride with methanol, the reaction occurs in a solvent; and the maleic anhydride and solvent are present in amounts that provide a molar ratio of the maleic anhydride to solvent in the range of about 1 to 1.2, about 1 to 1.3, or about 1 to 1.4

In one embodiment, with respect to the reaction of maleic anhydride with methanol, the reaction occurs in a solvent; and the maleic anhydride and solvent are present in amounts that provide a molar ratio of the maleic anhydride to solvent of around 1 to 1.3.

In one embodiment, with respect to the reaction of maleic anhydride with methanol, the reaction occurs at a temperature from about 15° C. to about 100° C., about 20° C. to about 80° C., about 30° C. to about 80° C., about 40° C. to about 80° C., or about 50° C. to about 70° C.

In another embodiment, with respect to the reaction of maleic anhydride with methanol, the reaction occurs at a temperature from about 20° C. to about 80° C.

In yet another embodiment, with respect to the reaction of maleic anhydride with methanol, the reaction occurs at a temperature from about 30° C. to about 80° C.

In yet another embodiment, with respect to the reaction of maleic anhydride with methanol, the reaction occurs at a temperature from about 40° C. to about 80° C.

In yet another embodiment, with respect to the reaction of maleic anhydride with methanol, the reaction occurs at a temperature from about 50° C. to about 70° C.

In a particular embodiment, with respect to the reaction of maleic anhydride with methanol, the reaction occurs at about 50° C. to about 70° C.

In a particular embodiment, with respect to the reaction of maleic anhydride with methanol, the reaction occurs at a temperature of around 60° C.

In one embodiment, with respect to the reaction of maleic anhydride with methanol, the reaction occurs over a period of about 1 hour to 140 hours.

In another embodiment, with respect to the reaction of maleic anhydride with methanol, the reaction occurs over a period of about 1 hour to 24 hours.

In another embodiment, with respect to the reaction of maleic anhydride with methanol, the reaction occurs over a period of about 1 hour to 20 hours.

In a particular embodiment, with respect to the reaction of maleic anhydride with methanol, the reaction occurs over a period of about 1 hour to 15 hours.

In another particular embodiment, with respect to the reaction of maleic anhydride with methanol, the reaction occurs over a period of about 1 hour to 5 hours. In a more particular embodiment, the reaction occurs over a period of about 2 hours to 4 hours. In a most particular embodiment, the reaction occurs over a period of about 3 hours.

In a more particular embodiment, with respect to the reaction of maleic anhydride with methanol, the reaction occurs at a temperature of around 60° C., and over a period of about 3 hours.

In one embodiment, with respect to the process, after the completion of the reaction of maleic anhydride with methanol, the mixture is concentrated; and the resulting concentrate containing the crude monomethyl maleate is used as such for the reaction with the compound of formula (II).

In one embodiment, with respect to the process, after the completion of the reaction of maleic anhydride with methanol, the mixture is concentrated; and the resulting concentrate is diluted with a solvent; and the solution is used as such for the reaction with the compound of formula (II). In one embodiment, the solvent is any solvent useful for the reaction of monomethyl maleate with the compound of formula (II), as described herein. In a particular embodiment, the solvent is toluene or acetonitrile.

In one embodiment, with respect to the process, the crude product from the reaction of maleic anhydride with methanol is carried forward for the reaction of monomethyl maleate with the compound of formula (II) without any further purification.

In one embodiment, with respect to the process, the crude product from the reaction of maleic anhydride with methanol is not isolated.

In another embodiment, the product from the reaction of maleic anhydride with methanol is used for the reaction of monomethyl maleate with the compound of formula (II) as a concentrated solution.

In another aspect, the present disclosure provides a one-pot process for preparing monomethyl fumarate (MMF). The process comprises the steps of
(i) reacting maleic anhydride with methanol to form monomethyl maleate; and
(ii) reacting the monomethyl maleate with a compound of formula (II)

(II)

to produce MMF; wherein $R^1$ is selected from unsubstituted $C_1$-$C_6$ alkyl, unsubstituted $C_3$-$C_6$ cycloalkyl, substituted $C_1$-$C_6$ alkyl and substituted $C_3$-$C_6$ cycloalkyl; and the substitution is selected from halo and $C_1$-$C_6$ alkoxy.

In one embodiment, with respect to the one-pot process, the reaction of step (i) occurs in the absence of a solvent. In another embodiment, the reaction of step (i) occurs in the presence of a solvent.

In one embodiment, with respect to the one-pot process, the reaction of step (ii) occurs in the presence of a solvent.

In one embodiment, with respect to the one-pot process, the process comprises the steps of:
(a) reacting maleic anhydride with methanol to obtain a reaction mixture containing monomethyl maleate;
(b) concentrating the reaction mixture to obtain a monomethyl maleate concentrate;
(c) diluting the monomethyl maleate concentrate with a solvent; and
(d) reacting the solvent-diluted monomethyl maleate concentrate with a compound of formula (II)

(II)

to produce MMF; wherein $R^1$ is selected from unsubstituted $C_1$-$C_6$ alkyl, unsubstituted $C_3$-$C_6$ cycloalkyl, substituted $C_1$-$C_6$ alkyl and substituted $C_3$-$C_6$ cycloalkyl; and the substitution is selected from halo and $C_1$-$C_6$ alkoxy.

In one embodiment, with respect to the compound of formula (II), $R^1$ is as described herein. In another embodiment, R¹ is Me, Et, n-Pr, i-Pr, n-Bu, i-Bu, sec-Bu, or t-Bu. In yet another embodiment, R¹ is cyclopropyl or cyclobutyl.

In one embodiment, with respect to the reaction of step (a), the reaction occurs in absence of any solvent. In another embodiment, with respect to the reaction of step (a), the reaction occurs in a solvent. In one embodiment, the solvent is selected from the group consisting of acetonitrile, benzonitrile, hexane, heptane, toluene, xylene, anisole, cumene, chlorobenzene, cyclohexane, methylcyclohexane, ethyl acetate, dichloromethane, dichloroethane, trichloroethane, tetrachloroethane, tetrahydrofuran, diphenyl ether, methyl tert-butyl ether, dioxane, dimethoxyethane, diethoxyethane, dibutyl ether, diisopropyl ether, and combinations thereof.

In a particular embodiment, with respect to the reaction of step (a), the reaction occurs in a solvent; and the solvent is toluene. In another particular embodiment, the solvent is acetonitrile.

In one embodiment, with respect to the reaction of step (a), the reaction occurs in a solvent; and the maleic anhydride and solvent are present in amounts that provide a molar ratio of the maleic anhydride to solvent in the range of about 1 to 25 to about 1 to 0.1. In another embodiment, the ratio is in the range of about 1 to 1.2 to about 1 to 1.4.

In one embodiment, with respect to the reaction of step (a), the reaction occurs in a solvent; and the maleic anhydride and solvent are present in amounts that provide a molar ratio of the maleic anhydride to solvent in the range of about 1 to 25, about 1 to 20, about 1 to 15, about 1 to 10, about 1 to 8, about 1 to 5, about 1 to 4, about 1 to 3, about 1 to 2, about 1 to 1, about 1 to 0.9, about 1 to 0.8, about 1 to 0.7, about 1 to 0.6, about 1 to 0.5, about 1 to 0.4, about 1 to 0.3, about 1 to 0.2 or about 1 to 0.1, about 1 to 0.6 or about 1 to 0.5, about 1 to 0.4, about 1 to 0.3, about 1 to 0.2 or about 1 to 0.1. In a particular embodiment, the molar ratio of the maleic anhydride to solvent is in the range of about 1 to 1, about 1 to 0.95, about 1 to 0.90, about 1 to 0.85, about 1 to 0.80, about 1 to 0.75, or about 1 to 0.70. In a more particular embodiment, the molar ratio is around 1 to 0.80.

In a particular embodiment, with respect to the reaction of step (a), the reaction occurs in toluene, and the molar ratio of maleic anhydride to toluene is about 1 to 3.

In a particular embodiment, with respect to the reaction of step (a), the reaction occurs in toluene, and the molar ratio of maleic anhydride to toluene is about 1 to 0.80. In one embodiment, with respect to the reaction of step (a), the reaction occurs in a solvent; and the maleic anhydride and solvent are present in amounts that provide a molar ratio of the maleic anhydride to solvent in the range of about 1 to 0.98, about 1 to 0.99, about 1 to 1, about 1 to 1.10, about 1 to 1.15, about 1 to 1.20, about 1 to 1.30, or about 1 to 1.40, or about 1 to 1.50, about 1 to 1.60, about 1 to 1.70, or about 1 to 1.80, about 1 to 1.90, about 1 to 2.00, about 1 to 2.10, about 1 to 2.20, about 1 to 2.30, about 1 to 2.40, about 1 to 2.50, about 1 to 2.60, about 1 to 2.70, about 1 to 2.80, about 1 to 2.90, or about 1 to 3.00.

In one embodiment, with respect to the reaction of step (a), the reaction occurs in a solvent; and the maleic anhydride and solvent are present in amounts that provide a molar ratio of the maleic anhydride to solvent in the range of about 1 to 1.2, about 1 to 1.3, or about 1 to 1.4

In one embodiment, with respect to the reaction of step (a), the reaction occurs in a solvent; and the maleic anhydride and solvent are present in amounts that provide a molar ratio of the maleic anhydride to solvent of around 1 to 1.3.

In one embodiment, with respect to the reaction of step (a), the reaction occurs at a temperature from about 15° C. to about 100° C., about 20° C. to about 80° C., about 30° C. to about 80° C., about 40° C. to about 80° C., or about 50° C. to about 70° C.

In another embodiment, with respect to the reaction of step (a), the reaction occurs at a temperature from about 20° C. to about 80° C.

In yet another embodiment, with respect to the reaction of step (a), the reaction occurs at a temperature from about 30° C. to about 80° C.

In yet another embodiment, with respect to the reaction of step (a), the reaction occurs at a temperature from about 40° C. to about 80° C.

In yet another embodiment, with respect to the reaction of step (a), the reaction occurs at a temperature from about 50° C. to about 70° C.

In a particular embodiment, with respect to the reaction of step (a), the reaction occurs at about 50° C. to about 70° C.

In a particular embodiment, with respect to the reaction of step (a), the reaction occurs at a temperature of around 60° C.

In one embodiment, with respect to the reaction of step (a), the reaction occurs over a period of about 1 hour to 140 hours.

In another embodiment, with respect to the reaction of step (a), the reaction occurs over a period of about 1 hour to 24 hours.

In another embodiment, with respect to the reaction of step (a), the reaction occurs over a period of about 1 hour to 20 hours.

In a particular embodiment, with respect to the reaction of step (a), the reaction occurs over a period of about 1 hour to 15 hours.

In another particular embodiment, with respect to the reaction of step (a), the reaction occurs over a period of about 1 hour to 5 hours. In a more particular embodiment, the reaction occurs over a period of about 2 hours to 4 hours. In a most particular embodiment, the reaction occurs over a period of about 3 hours.

In a more particular embodiment, with respect to the reaction of step (a), the reaction occurs at a temperature of around 60° C., and over a period of about 3 hours.

In one embodiment, with respect to the reaction of step (b), the reaction mixture is concentrated by removing volatile material(s) from the reaction mixture. In another embodiment, the reaction mixture is concentrated by partially removing volatile material(s) from the reaction mixture. In one embodiment, the volatile material(s) is/are removed under vacuum. In one embodiment, the volatile material(s) comprises unreacted methanol and/or the reaction solvent.

In one embodiment, with respect to the one-pot process, the reaction of step (ii) or the step (c) occur in the presence of a solvent. In one embodiment, with respect to the reaction of step (ii) or step (c), the solvent is selected from the group consisting of acetonitrile, benzonitrile, hexane, heptane, toluene, xylene, anisole, cumene, chlorobenzene, cyclohexane, methylcyclohexane, ethyl acetate, dichloromethane, dichloroethane, trichloroethane, tetrachloroethane, tetrahydrofuran, diphenyl ether, methyl tert-butyl ether, dioxane, dimethoxyethane, diethoxyethane, dibutyl ether, diisopropyl ether, and combinations thereof. In a particular embodiment, the solvent is selected from toluene and acetonitrile. In a more particular embodiment, the solvent is toluene.

In one embodiment, the solvent-diluted monomethyl maleate concentrate is a solution. In another embodiment, the solvent-diluted monomethyl maleate concentrate is a suspension.

In one embodiment, with respect to the reaction of step (ii) or step (c), the monomethyl maleate and solvent are present in amounts to provide a molar ratio of the monomethyl maleate to solvent in a range of about 1 to 50 to about 1 to 1. In another embodiment, the ratio of monomethyl maleate to solvent is in a range of about 1 to 50, about 1 to 25, about 1 to 20, about 1 to 15, about 1 to 10, about 1 to 8, about 1 to 5, about 1 to 4, about 1 to 3, about 1 to 2, or about 1 to 1. In a particular embodiment, the molar ratio is in a range of about 1 to 2.

In one embodiment, with respect to the reaction of step (ii) or step (c), the solvent is in toluene; and the molar ratio of the monomethyl maleate to toluene is about 1 to 3.

In one embodiment, with respect to the reaction of step (ii) or step (c), the solvent is in toluene; and the molar ratio of the monomethyl maleate to toluene is about 1 to 2.

In one embodiment, with respect to the reaction of step (ii) or the reaction of step (d), the monomethyl maleate and the compound of formula (II) are present in amounts to provide a molar ratio of the monomethyl maleate to the compound of formula (II) in a range of about 1 to 0.010 to about 1 to 1. In another embodiment, the molar ratio is in a range of about 1 to 0.010, about 1 to 0.015, about 1 to 0.020, about 1 to 0.025, about 1 to 0.030, about 1 to 0.035, about 1 to 0.040, or about 1 to 0.045, about 1 to 0.050, about 1 to 0.055, about 1 to 0.060, about 1 to 0.065, about 1 to 0.070, or about 1 to 0.075, about 1 to 0.080, about 1 to 0.085, about 1 to 0.090, about 1 to 0.095, about 1 to 0.100, about 1 to 0.105, about 1 to 0.110, about 1 to 0.115, about 1 to 0.120, about 1 to 0.125, about 1 to 0.130, about 1 to 0.135, about 1 to 0.140, about 1 to 0.145, about 1 to 0.150, about 1 to 0.160, about 1 to 0.170, about 1 to 0.180, about 1 to 0.190, or about 1 to 0.200. In yet another embodiment, the molar ratio is in a range of about 1 to 0.250, about 1 to 0.300, about 1 to 0.350, about 1 to 0.400, about 1 to 0.450, about 1 to 0.500, about 1 to 0.550, about 1 to 0.600, about 1 to 0.650, about 1 to 0.700, about 1 to 0.750, about 1 to 0.800, about 1 to 0.850, about 1 to 0.900, about 1 to 0.950, or about 1 to 1. In a particular embodiment, the molar ratio is in a range of about 1 to 0.010. In a more particular embodiment, the molar ratio is in a range of about 1 to 0.10.

In one embodiment, with respect to the reaction of step (ii) or the reaction of step (d), the compound of formula (II) is present in a amount of about 1 to 100 mole % of the monomethyl maleate. In another embodiment, the compound of formula (II) is present in a amount of about 1 to 80 mole %, about 1 to 70 mole %, about 1 to 60 mole %, about 1 to 50 mole %, about 1 to 40 mole %, about 1 to 30 mole %, about 1 to 20 mole %, about 1 to 20 mole %, about 1 to 10 mole %, about 1 to 5 mole %, or about 1 to 3 mole %, of the monomethyl maleate. In a particular embodiment, the compound of formula (II) is present in a amount of about 1 to 20 mole % of the monomethyl maleate. In another particular embodiment, the compound of formula (II) is present in a amount of about 1 to 15 mole % of the monomethyl maleate. In another particular embodiment, the compound of formula (II) is present in a amount of about 1 to 10 mole % of the monomethyl maleate. In another particular embodiment, the compound of formula (II) is present in a amount of about 1 to 5 mole % of the monomethyl maleate.

In one embodiment, with respect to the reaction of step (ii) or the reaction of step (d), the reaction occurs at a temperature ranging from about 50° C. to about 100° C. In another embodiment, the reaction occurs at a temperature ranging from about 50° C. to about 100° C., 60° C. to about 100° C., 60° C. to about 90° C., 70° C. to about 90° C., 70° C. to about 85° C., or about 80° C. to about 85° C. In another embodiment, the reaction occurs at a temperature ranging from about 60° C. to about 90° C. In another embodiment, the reaction occurs at a temperature ranging from about 70° C. to about 90° C. In another embodiment, the reaction occurs at a temperature ranging from about 70° C. to about 85° C. In another embodiment, the reaction occurs at a temperature ranging from about 80° C. to about 85° C. In a particular embodiment, the reaction occurs at a temperature of about 85° C.

In one embodiment, with respect to the reaction of step (ii) or the reaction of step (d), the reaction occurs over a period of about 2 to 140 hours. In another embodiment, the reaction occurs over a period of about 2 hours to 24 hours. In another embodiment, the reaction occurs over a period of about 2 hours to 20 hours. In another embodiment, the reaction occurs over a period of about 4 hours to 15 hours. In a particular embodiment, the reaction occurs over a period of about 10 hours to 16 hours. In a more particular embodiment, the reaction occurs over a period of about 14 hours.

In one embodiment, with respect to the compound of formula (II), the compound is MeC(O)Cl, EtC(O)Cl, n-Pr—C(O)Cl, i-Pr—C(O)Cl, n-Bu-C(O)Cl, i-Bu-C(O)Cl, sec-Bu-C(O)Cl, or t-Bu-C(O)Cl.

In one embodiment, with respect to the compound of formula (II), the compound is acetyl chloride, propanoyl chloride, butanoyl chloride, pentanoyl chloride, or pivaloyl chloride.

In one embodiment, with respect to the compound of formula (II), the compound is cyclopropyl chloride, cyclobutyl chloride, cyclopentyl chloride, or cyclohexyl chloride.

In a particular embodiment, with respect to the compound of formula (II), the compound is MeC(O)Cl or acetyl chloride.

In one particular embodiment, with respect to the reaction of step (ii) or the reaction of step (d), the reaction occurs in toluene, the MMF and toluene are present in amounts to provide a molar ratio of the monomethyl maleate to the toluene of about 1 to 3; the compound of formula (II) is acetyl chloride; the reaction occurs (i) in the presence of about 10 mole % of acetyl chloride, (ii) for a period of about 14 hours, and (iii) at a temperature of about 85° C.

In one particular embodiment, with respect to the reaction of step (ii) or the reaction of step (d), the reaction occurs in toluene, the MMF and toluene are present in amounts to provide a molar ratio of the monomethyl maleate to the toluene of about 1 to 2; the compound of formula (II) is acetyl chloride; the reaction occurs (i) in the presence of about 10 mole % of acetyl chloride, (ii) for a period of about 14 hours, and (iii) at a temperature of about 85° C.

In the processes of the present disclosure, with respect to the reaction of monomethyl maleate and the compound of formula (II), when the compound of formula (II) is acetyl chloride, the reaction produces volatile byproducts such as methyl acetate and acetic acid. Thus, these byproducts can easily be removed during product isolation, for example by simple distillation under reduced pressure. In particular embodiments, the product may be crystallized by cooling the solution without any additional purification.

In one embodiment, MMF prepared following the above processes is used to prepare a prodrug of MMF.

Thus, in certain aspect, the present disclosure provides the use of MMF in preparation of the prodrugs of MMF.

In a further aspect, the present disclosure provides processes to prepare prodrugs of MMF.

In one embodiment, with respect to the process for preparation of the prodrug, the process comprises reacting the MMF with a compound of formula (IV) to produce an MMF prodrug of formula (V):

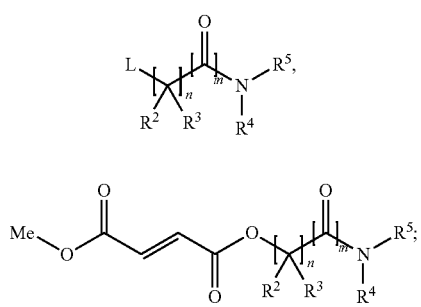

(IV)

(V)

wherein L is a leaving group; each $R^2$ and $R^3$ is independently H, $C_{1-6}$ alkyl, or substituted $C_{1-6}$ alkyl;
each $R^4$ and $R^5$ is independently H, $C_{1-6}$ alkyl, or substituted $C_{1-6}$ alkyl; or
$R^4$ and $R^5$, together with the nitrogen to which they are attached, form a 5-10 membered heteroalkyl ring; m is 0 or 1; and n is an integer from 1 to 6; provided that when m is 0, then n is an integer from 2 to 6.

In one embodiment, with respect to formula (IV), L is halo, OH, O-tosylate, or O-mesylate.

In one embodiment, with respect to formula (IV) or (V), n is 1. In another embodiment, each of n and m is 1.

In one embodiment, with respect to formula (IV) or (V), n is an integer from 2 to 6. In another embodiment, n is an integer from 2 to 6; and m is 0 or 1.

In one embodiment, with respect to formula (IV) or (V), each $R^2$ and $R^3$ is independently H.

In one embodiment, with respect to formula (IV) or (V), each $R^4$ and $R^5$ is independently Me, Et, n-Pr, i-Pr, n-Bu, i-Bu, sec-Bu, t-Bu, n-pentyl, or n-hexyl.

In one embodiment, with respect to formula (IV) or (V), $R^4$ and $R^5$, together with the nitrogen to which they are attached to, form a morpholino, pyrrolidino, or piperidino ring.

In one embodiment, the MMF prodrug is selected from:

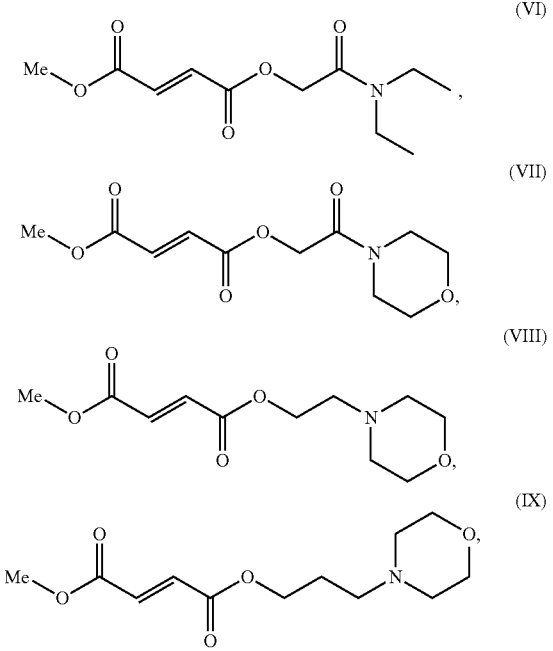

(VI)

(VII)

(VIII)

(IX)

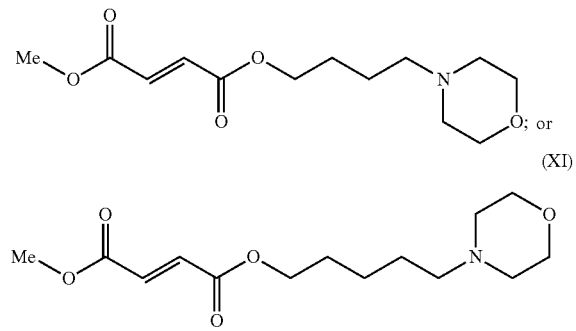

(X)

(XI)

and pharmaceutically acceptable salts of any of the foregoing.

In one embodiment, the MMF prodrug is selected from:
N,N-diethylcarbamoyl)methyl methyl (2E)but-2-ene-1,4-dioate;
methyl 2-morpholin-4-yl-2-oxoethyl (2E)but-2-ene-1,4-dioate;
methyl 2-morpholin-4-ylethyl (2E)but-2-ene-1,4-dioate;
methyl 3-morpholin-4-ylpropyl (2E)but-2-ene-1,4-dioate;
methyl 4-morpholin-4-ylbutyl (2E)but-2-ene-1,4-dioate; and
methyl 5-morpholin-4-ylpentyl (2E)but-2-ene-1,4-dioate;
and pharmaceutically acceptable salts of any of the foregoing.

In one embodiment, the process may further comprise recrystallizing the MMF prodrug. In another embodiment, the MMF prodrug may be substantially free of toxic impurities.

Additional embodiments within the scope of the present disclosure are set forth in non-limiting fashion elsewhere herein and in the examples. It should be understood that these examples are for illustrative purposes only and are not to be construed as limiting this invention in any manner.

Synthesis

Starting materials useful for preparing compounds and intermediates thereof and/or practicing methods described herein are commercially available or can be prepared by well-known synthetic methods. The methods presented in the schemes provided by the present disclosure are illustrative rather than comprehensive. It will be apparent to those skilled in the art that many modifications, both to materials and methods, may be practiced without departing from the scope of the disclosure.

General Experimental Protocols

All reagents and solvents that are purchased from commercial suppliers are used without further purification or manipulation procedures.

Proton NMR (400 MHz) and carbon NMR spectra (125 MHz) are recorded on a Varian AS 400 NMR spectrometer equipped with an autosampler and data processing software. $CDCl_3$ (99.8% D), DMSO-$d_6$ (99.9% D), or MeOH-$d_4$ (99.8+% D), and acetonitrile-$d_3$ are used as solvents unless otherwise noted. The $CHCl_3$, DMSO-$d_5$, or MeOH-$d_3$ solvent signals are used for calibration of the individual spectra. Analytical thin layer chromatography (TLC) is performed using a Whatman, Schleicher & Schuell TLC and MK6F silica gel plates (2.5×7.5 cm, 250 µm layer thickness). Melting points are recorded in glass capillaries using a Stanford Research Systems (SRS) Optimelt Automated Melting Point System, S/N 78047. Analytical LC/MS is performed on a Waters 2790 separation module equipped with a Waters Micromass QZ mass spectrometer, a Waters 996 photodiode detector, and a Merck Chromolith UM2072-027 or Phenomenex Luna C-18 analytical column. Mass-guided preparative HPLC purification of final compounds is performed using an instrument equipped with a Waters 600 controller, ZMD Micromass spectrometer, a Waters 2996 photodiode array detector, and a Waters 2700 Sample Manager. Acetonitrile/water gradients containing 0.05% formic acid are used as eluents in both analytical and preparative HPLC experiments. Compound isolation from aqueous solvent mixtures, e.g., acetonitrile/water/0.05% formic acid, is accomplished by primary lyophilization (freeze drying) of the frozen solutions under reduced pressure at room temperature using manifold freeze dryers such as a Heto Drywinner DW 6-85-1, a Heto FD4, or a VIRTIS Freezemobile 25 ES equipped with high vacuum pumps.

Chemical names are generated with the Chemistry 4-D Draw Pro Version 7.01c (Draw Chemical Structures Intelligently© 1993-2002) from ChemInnovation Software, Inc., San Diego, USA).

Non-commercially available starting materials are synthesized from commercially available starting materials, and by adapting methods well known in the art.

General Synthetic Procedures

The compounds of formula (I) can be prepared from readily available starting materials using the following general methods and procedures. See, e.g., Synthetic Scheme, below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

Synthesis of Monomethyl Fumarate

The compound of formula (I), for example, may be prepared by the reaction of maleic anhydride with methanol followed by the isomerization of the intermediate monomethyl maleate in the presence an acid chloride. The final product, monomethyl fumarate or the compound of formula (I) can be isolated and purified by known standard procedures known to one skilled in the art of organic synthesis. Such standard purification procedures include (but are not limited to) recrystallization, column chromatography or HPLC. The following scheme is presented with details as to the preparation of monomethyl fumarate.

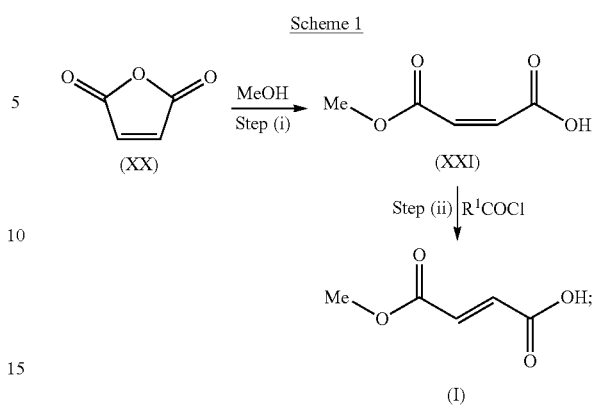

Scheme 1 and wherein $R^1$ is as described herein.

The syntheses of monomethyl fumarate is carried out in accordance with the methods set forth above and using the appropriate reagents, starting materials, and purification methods known to those skilled in the art. All starting materials in the following general syntheses may be commercially available or obtained by conventional methods known to those skilled in the art. All reactions are carried out under nitrogen atmosphere.

Representative Procedures

One-Pot Process for Preparation of Monomethyl Fumarate

Example 1

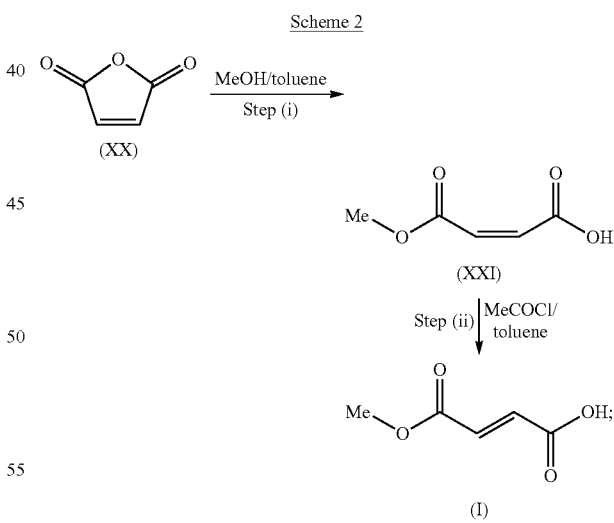

Scheme 2

Step (i)

A mixture of maleic anhydride (4.985 kg, 50.8 mol), toluene (4.2 L), and methanol (3.33 L) was stirred at 60° C. for 3 hours. After cooling, the mixture was concentrated under vacuum to remove about 3 L of volatile material. Toluene (4 L) was added and the mixture was concentrated under vacuum to remove about 4 L of volatile material. Another 4 L of toluene is added, and the mixture was concentrated to remove about 4 L of volatile material. The resulting mixture was then diluted with 10 L of toluene, and the solution was carried forward to the next step.

Step (ii)

The toluene solution from Step (i) was treated with acetyl chloride (367 mL, 406 g, 5.17 mol) and the mixture was heated to 80° C. After stirring the reaction mixture around 80° C. for 14 hr, the mixture was diluted with 16 L of toluene and cooled to 20-25° C. The precipitated product was collected by filtration, rinsed with toluene and dried under vacuum at 40-45° C. for 14 hours to afford the pure monomethyl fumarate as white crystalline solid (5.1 kg).

MP 145.4-145.8° C.; MS (ESI): m/z 128.8 (Calcd. 130.1); $^1$H NMR (DMSO-$d_6$), δ 13.25 (s, 1H), 6.71 (s, 2H), 3.74 (s, 3H).

Example 2

Step (i)

A mixture of maleic anhydride (98.06 g, 1 mol), toluene (0.5 L), and methanol [34.87 g, in three portions—32.5 g (after 72 hr), 0.79 g (after 96 hr), and 1.58 g (after 120 hr)] was stirred at 20° C. for 144 hours. The resulting mixture was then carried forward to the next step.

Step (ii)

The toluene solution from Step (i) was treated with acetyl chloride (0.75 mL, 828 mg, 0.11 mol, 1.1 mole % of the SM) and the mixture was heated to 85° C. After stirring the reaction mixture around 85° C. for 24 hr, more acetyl chloride (0.75 mL, 828 mg, 0.11 mol, 1.1% of the SM) was added and the stirring continued for another 20 hours. After cooling, the precipitated product was collected by filtration, rinsed with toluene and dried under vacuum at 40-45° C. for 14 hours to afford the pure monomethyl fumarate as white crystalline solid.

Example 3

Step (i)

A mixture of maleic anhydride (196.1 g, 2 mol), toluene (1 L), and methanol (70.5 g, 89.2 mL, 2.2 mol) was stirred at 22.6° C. for 12 hr, and then at 30° C. for additional 24 hours. More methanol (3.96 g, 5 mL, 0.12 mol) was added and the stirring was continued for another 20 hours. The resulting mixture was then carried forward to the next step.

Step (ii)

The toluene solution from Step (i) was treated with acetyl chloride (3 mL, 3.3 g, 42 mmol, 2.1 mole % of the monomethyl maleate) and the mixture was heated to 85° C. After stirring the reaction mixture around 85° C. for 6 hr, the mixture was cooled; and the precipitated product was collected by filtration, rinsed with toluene and dried under vacuum at 70° C. for 2 hours to afford the pure monomethyl fumarate as white crystalline solid (178.5 g).

Example 4

Step (i)

A mixture of maleic anhydride (196.1 g, 2 mol), toluene (1 L), and methanol (75 g, 95 mL, 2.34 mol) was stirred at 30° C. for 12 hr, and then at 50° C. for 2 hr, and finally at 60° C. for additional 1 hour. More methanol (3.96 g, 5 mL, 0.12 mol) was added and the stirring was continued at 60° C. for another 36 hours. The resulting mixture is then carried forward to the next step.

Step (ii)

The toluene solution from Step (i) was treated with acetyl chloride (4 mL, 4.4 g, 56 mmol, 2.8 mole % of the SM) and the mixture was heated to 60° C. After stirring the reaction mixture around 60° C. for 24 hr, the mixture was cooled; and the precipitated product was collected by filtration, rinsed with toluene and dried under vacuum at 70° C. for 2 hours to afford the pure monomethyl fumarate as white crystalline solid (179.4 g).

Example 5

Step (i)

A mixture of maleic anhydride (300 g, 3.06 mol), toluene (1.5 L), and methanol (70.5 g, 89.2 mL, 2.2 mol) were stirred at 60° C. for 14 hours. After cooling, the mixture was concentrated under vacuum to a volume of 1.6 L. Toluene was added to make the total volume of 2 L and the solution was carried forward to the next step.

Step (ii)

The toluene solution from Step (i) is treated with acetyl chloride (6 mL, 6.63 g, 84 mmol, 2.75 mole % of the SM) and the mixture was heated to 40° C. After stirring the reaction mixture around 40° C. for 34 hr, the mixture was cooled; and the precipitated product was collected by filtration, rinsed with toluene and dried under vacuum at 70° C. for 2 hours to afford the pure monomethyl fumarate as white crystalline solid (135.9 g).

Example 6

Step (i)

A mixture of maleic anhydride (300 g, 3.06 mol), toluene (1.5 L), and methanol (158 g, 200 mL, 4.93 mol) was stirred at 60° C. for 16 hours. After cooling, the mixture was concentrated under vacuum to a volume of 1.2 L. Toluene was added to make the total volume of 2 L and the solution was carried forward to the next step.

Step (ii)

The toluene solution from Step (i) was treated with acetyl chloride (3 mL, 3.32 g, 42 mmol; in 1 mL portions) and the mixture was heated to 60° C. After stirring the reaction mixture around 60° C. for 7 hr, the mixture was cooled; and the precipitated product was collected by filtration, rinsed with toluene and dried under vacuum at 70° C. for 2 hours to afford the pure monomethyl fumarate as white crystalline solid (321.6 g).

Example 7

Step (i)

A mixture of maleic anhydride (600 g, 6.12 mol), toluene (1 L), and methanol (316.4 g, 400 mL, 9.87 mol) was stirred at 60° C. for 2 hours. After cooling, the mixture was concentrated under vacuum to a volume of 1.25 L. Toluene was added to make the total volume of 1.9 L and the solution was carried forward to the next step.

Step (ii)

The toluene solution from Step (i) was treated with acetyl chloride (6 mL, 6.63 g, 84 mmol, 1.4 mole %) and the mixture was heated to 50° C. After stirring the reaction mixture around 50° C. for 16 hr, more acetyl chloride (6 mL, 6.63 g, 84 mmol, 1.4%) was added and the stirring continued at the same temperature for 6 hours. The mixture was cooled and the precipitated product was collected by filtration, rinsed with toluene and dried under vacuum at 70° C. for 2 hours to afford the pure monomethyl fumarate as white crystalline solid (362 g).

Example 8

Step (i)

A mixture of maleic anhydride (600 g, 6.12 mol), toluene (1 L), and methanol (316.4 g, 400 mL, 9.87 mol) was stirred at 60° C. for 7 hours. After cooling, the mixture was concentrated under vacuum to a volume of 1 L. Toluene was added to make the total volume of 1.9 L and the solution was carried forward to the next step.

Step (ii)

The toluene solution from Step (i) was treated with acetyl chloride (22 mL, 24.3 g, 310 mmol, 5 mole %) and the mixture was heated to 50° C. After stirring the reaction mixture around 50° C. for 12 hr, the mixture was cooled and the precipitated product was collected by filtration, rinsed with toluene and dried under vacuum at 40° C. for 24 hours to afford the pure monomethyl fumarate as white crystalline solid (440 g).

Example 9

Step (i)

A mixture of maleic anhydride (600 g, 6.12 mol), and toluene (0.5 L) was heated to at 60° C., and treated with methanol (316.4 g, 400 mL, 9.87 mol) over a period of 1 hour. After cooling, the mixture was concentrated under vacuum to a volume of 0.9 L. Toluene was added to make the total volume of 1.375 L and the solution was carried forward to the next step.

Step (ii)

The toluene solution from Step (i) was treated with acetyl chloride (19.9 mL, 22 g, 280 mmol, 4.6 mole %) and the mixture was heated to 50° C. After stirring the reaction mixture around 50° C. for 16 hr, the mixture was cooled and the precipitated product as collected by filtration, rinsed with toluene and dried under vacuum at 50° C. for 24 hours to afford the pure monomethyl fumarate as white crystalline solid (634 g).

Example 10

Step (i)

A mixture of maleic anhydride (600 g, 6.12 mol), toluene (0.5 L), and methanol (316.4 g, 400 mL, 9.87 mol) was stirred at 60° C. for 2 hours. After cooling, the mixture was concentrated under vacuum to remove about 275 mL of volatiles. Toluene (500 mL) was added and the mixture was concentrated under vacuum to remove about 500 mL of volatiles. Toluene was added to make the total volume of 1 L and the solution was carried forward to the next step.

Step (ii)

The toluene solution from Step (i) was treated with acetyl chloride (44 mL, 48.62 g, 620 mmol, 10.1 mole %) and the mixture was heated to 80° C. After stirring the reaction mixture around 80° C. for 12 hr, the mixture was cooled and the precipitated product was collected by filtration, rinsed with toluene and dried under vacuum at 40° C. for 24 hours to afford the pure monomethyl fumarate as white crystalline solid (613 g).

Example 11

Recrystallization of Monomethyl Fumarate

A mixture of monomethyl fumarate (1.551 kg) and methanol (3 L) was heated to 60° C. and cooled slowly to 10° C. over a period of 20 hours. The precipitated product was collected by filtration, rinsed with methanol (400 mL) and dried under vacuum at 25° C. for 72 hours to afford the pure crystalline monomethyl fumarate as free-flowing white solid (1.1 kg).

Example 12

Preparation of the MMF Prodrug

N,N-Diethylcarbamoyl)methyl methyl (2E)but-2-ene-1,4-dioate

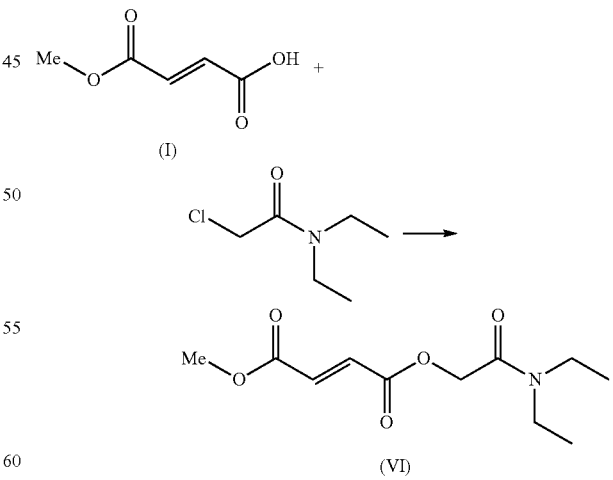

The diethylamino prodrug of MMF (VI) was prepared by reacting monomethyl fumarate (130 g, 1 mol) with 2-chloro-N,N-diethyl acetamide (157 g, 1.05 mol) in the presence of a base and following the procedure described in Gangakhedkar et al., U.S. Patent Publication No. 2010/0048651. Following concentration under vacuum, the purity by HPLC was 100.00% w/w, with 0.07% dimer.

Example 13

Preparation of the MMF Prodrug

Methyl 2-morpholin-4-yl-2-oxoethyl (2E)but-2-ene-1,4-dioate

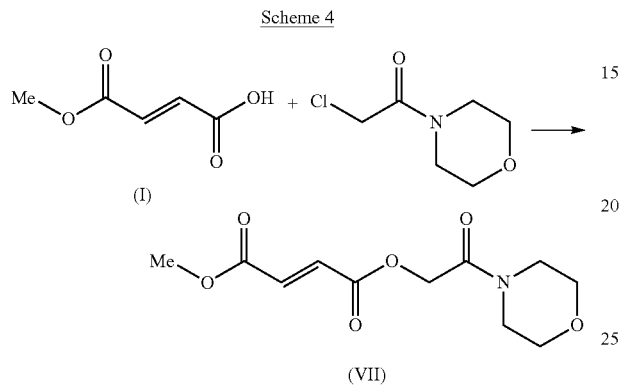

The morpholino prodrug of MMF (VII) is prepared by reacting of monomethyl fumarate (1 mol), with chloroacetyl-morpholine (1.05 mol) in the presence of a base and following the procedure described in Gangakhedkar et al., U.S. Patent Publication No. 2010/0048651.

Example 14

Preparation of the MMF Prodrug

Methyl 2-morpholin-4-ylethyl (2E)but-2-ene-1,4-dioate

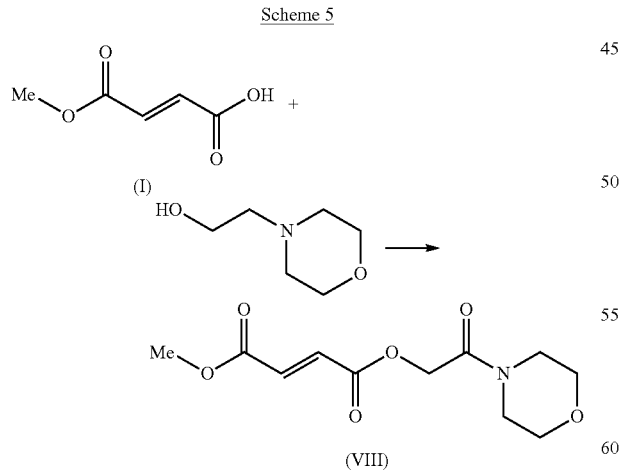

Monomethyl fumarate (MMF) was reacted with 1-ethyl-3-(3-dimethylaminopropyl)carbodiimide hydrochloride (EDAC) (1.2 eq) in dichloromethane (DCM) at ca. 0° C. 2-Morpholin-4-yl-ethyl-1-ol (1 eq) and 4-N,N-dimethylaminopyridine (DMAP) (catalytic amount) were added to the activated carboxylic acid. After the completion of the reaction, followed by the work-up of the reaction mixture, the title compound was isolated as a viscous oil.

Example 15

Preparation of the MMF Prodrug

Methyl 3-morpholin-4-ylpropyl (2E)but-2-ene-1,4-dioate

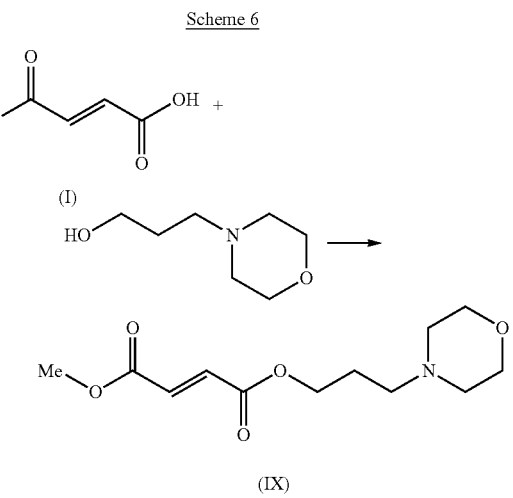

Monomethyl fumarate (MMF) was reacted with 1-ethyl-3-(3-dimethylaminopropyl)carbodiimide hydrochloride (EDAC) (1.2 eq) in dichloromethane (DCM) at ca. 0° C. 3-Morpholin-4-yl-propan-1-ol (1 eq) and 4-N,N-dimethylaminopyridine (DMAP) (catalytic amount) were added to the activated carboxylic acid. After the completion of the reaction, followed by the work-up of the reaction mixture, the title compound was isolated as a viscous-oil.

Example 16

Preparation of the MMF Prodrug

Methyl 4-morpholin-4-ylbutyl (2E)but-2-ene-1,4-dioate

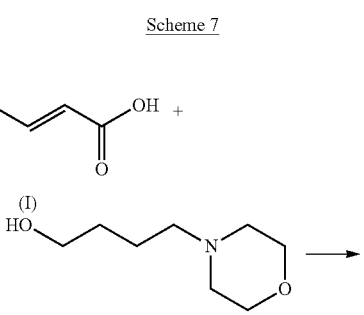

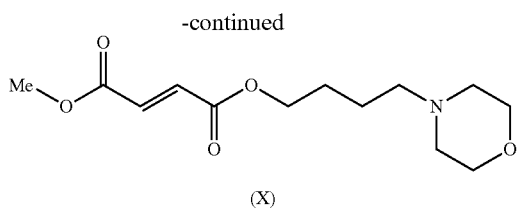

(X)

Monomethyl fumarate (MMF) was reacted with 1-ethyl-3-(3-dimethylaminopropyl)carbodiimide hydrochloride (EDAC) (1.2 eq) in dichloromethane (DCM) at ca. 0° C. 4-Morpholin-4-yl-butan-1-ol (1 eq) and 4-N,N-dimethylaminopyridine (DMAP) (catalytic amount) were added to the activated carboxylic acid. After the completion of the reaction, followed by the work-up of the reaction mixture, the title compound was isolated as a viscous-oil.

Example 17

Preparation of the MMF Prodrug

Methyl 5-morpholin-4-ylpentyl (2E)but-2-ene-1,4-dioate

Scheme 8

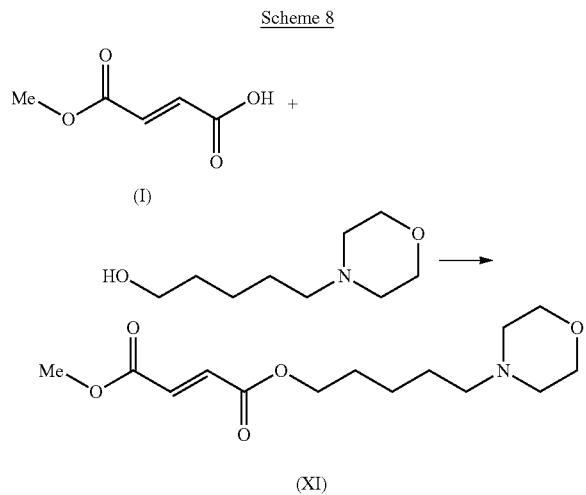

Monomethyl fumarate (MMF) was reacted with 1-ethyl-3-(3-dimethylaminopropyl)carbodiimide hydrochloride (EDAC) (1.2 eq) in dichloromethane (DCM) at ca. 0° C. 3-Morpholin-4-yl-propan-1-ol (1 eq) and 4-N,N-dimethylaminopyridine (DMAP) (catalytic amount) were added to the activated carboxylic acid. After the completion of the reaction, followed by the work-up of the reaction mixture, the title compound was isolated as a viscous oil.

Example 18

Step (i)

A 100-gallon reactor was charged with maleic anhydride (25 kg, 254.8 mol) and toluene (75 L). The resulting white suspension was heated slowly with a jacket set point of 60° C. under a nitrogen atmosphere. A solution of methanol (8.4 L) in toluene (12.5 L) was charged to the reaction mixture over 80 minutes, maintaining a temperature of at least 54° C. A second portion of a solution of methanol (8.4 L) in toluene (12.5 L) was charged to the reaction mixture over 40 minutes, maintaining a temperature between 54° C. and 63° C. The reaction mixture was stirred for 6 hours. The reactor was then cooled to room temperature and the reaction mixture was stirred overnight. The reaction mixture was concentrated to about 50 L, followed by addition of toluene (2×25 L) and additional distillation to remove 50 L of distillate. The concentrated reaction mixture was diluted with toluene (75 L).

Step (ii)

Acetyl chloride (0.2 eq, 4 kg, 51 mol) was added to the reaction mixture. The mixture was slowly heated to 83° C., and stirred for 6 hours and 10 minutes at a temperature of at least 80° C. The mixture was then cooled to room temperature. The solid product was filtered and washed with toluene (20 L). The product was dried on a pressure filter for one hour and then transferred to a 100-gallon reactor to which toluene was added (40 L). The resulting suspension was stirred at room temperature for 2 hours. The product was filtered and washed with toluene (20 L) followed by drying on a pressure filter for two days. The product was then dried in a conical dryer at temperatures between 40 and 42° C., resulting in 20.9 kg of desired product, monomethyl fumarate, with a purity of 99.97%.

Uses

Compounds of Formula (VI), (VII), (VIII), (IX), (X), and (XI) are prodrugs of monomethyl fumarate. These prodrugs and pharmaceutical compositions thereof may be administered to a patient suffering from any disease including a disorder, condition, or symptom for which monoalkyl hydrogen fumarates and/or fumaric acid esters are known or hereafter discovered to be therapeutically effective. Indications for which monomethyl fumarate (MMF) has been prescribed, and hence for which the prodrugs, or pharmaceutical compositions thereof are also expected to be effective, include psoriasis. Other indications for the prodrugs may be therapeutically effective include multiple sclerosis, irritable bowel disorder, ulcerative colitis, arthritis, chronic obstructive pulmonary disease, asthma, Parkinson's disease, Huntington's disease, and amyotrophic lateral sclerosis.

Methods of treating a disease in a patient provided by the present disclosure comprise administering to a patient in need of such treatment a therapeutically effective amount or dose of a prodrug. Compounds of Formula (VI), (VII), (VIII), (IX), (X), and (XI) or pharmaceutical compositions thereof may provide therapeutic or prophylactic plasma and/or blood concentrations of fumarate following administration to a patient.

The prodrugs of MMF may be included in a pharmaceutical composition and/or dosage form adapted for oral administration, although compounds of Formula (VI), (VII), (VIII), (IX), (X), or (XI) may also be administered by any other appropriate route, such as for example, by injection, infusion, inhalation, transdermally, or absorption through epithelial or mucosal membranes (e.g., oral, rectal, and/or intestinal mucosa).

The prodrugs of Formula (VI), (VII), (VIII), (IX), (X), or (XI) may be administered in an amount and using a dosing schedule as appropriate for treatment of a particular disease. Daily doses of compounds of Formula (VI), (VII), (VIII), (IX), (X), or (XI) may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, compounds of Formula (VI), (VII), (VIII), (IX), (X), or (XI) may be administered at a dose over time from about 1 mg to about 5 g per day, from about 10 mg to about 4 g per day, and in certain embodiments from about 20 mg to about 2 g per day. An appropriate dose of a compound Formula (VI), (VII), (VIII), (IX), (X), or (XI) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

Compounds of Formula (VI)-(XI) may be assayed in vitro and in vivo for the desired therapeutic or prophylactic activity prior to use in humans. In vivo assays, for example using appropriate animal models, may also be used to determine whether administration of a compound of Formula (VI)-(XI) is therapeutically effective.

Compounds of Formula (VI)-(XI) may be used to treat diseases, disorders, conditions, and symptoms of any of the foregoing for which alkyl hydrogen fumarates, such as MHF, are known to provide or are later found to provide therapeutic benefit. MHF is known to be effective in treating psoriasis, multiple sclerosis, an inflammatory bowel disease, asthma, chronic obstructive pulmonary disease, and arthritis. Hence, compounds of Formula (V)-(X) may also be used to treat any of these diseases and disorders. The underlying etiology of any of the foregoing diseases being treated may have a multiplicity of origins. Further, in certain embodiments, a therapeutically effective amount of one or more compounds of Formula (VI)-(XI) may be administered to a patient, such as a human, as a preventative measure against various diseases or disorders. Thus, a therapeutically effective amount of one or more compounds of Formula (VI)-(XI) may be administered as a preventative measure to a patient having a predisposition for and/or history of immunological, autoimmune, and/or inflammatory diseases including psoriasis, arthritis, asthma, and chronic obstructive pulmonary disease; cardiac insufficiency including left ventricular insufficiency, myocardial infarction, and angina pectoris; mitochondrial and neurodegenerative diseases such as Parkinson's disease, Alzheimer's disease, Huntington's disease, amyotrophic lateral sclerosis, retinopathia pigmentosa, and mitochondrial encephalomyopathy; transplantation rejection; autoimmune diseases such as multiple sclerosis; ischemia and reperfusion injury; AGE-induced genome damage; inflammatory bowel diseases such as Crohn's disease, irritable bowel disorder, and ulcerative colitis; and NF-κB mediated diseases.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, *Trends Mol Med* 2005, 11 (1), 43-48; and Mrowietz et al., *Br J Dermatology* 1999, 141, 424-429).

Inflammatory Arthritis

Inflammatory arthritis includes diseases such as rheumatoid arthritis, juvenile rheumatoid arthritis (juvenile idiopathic arthritis), psoriatic arthritis, and ankylosing spondylitis produce joint inflammation. The pathogenesis of immune-mediated inflammatory diseases including inflammatory arthritis is believed to involve TNF and NF-κB signaling pathways (Tracey et al., *Pharmacology & Therapeutics* 2008, 117, 244-279). DMF has been shown to inhibit TNF and inflammatory diseases including inflammatory arthritis, which are believed to involve TNF and NK-κB signaling, and therefore may be useful in treating inflammatory arthritis (Lowewe et al., *J Immunology* 2002, 168, 4781-4787).

Multiple Sclerosis

Multiple sclerosis (MS) is an inflammatory autoimmune disease of the central nervous system caused by an autoimmune attack against the insulating axonal myelin sheaths of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, *Lab Invest* 2001, 81, 263-281; and Virley, *NeuroRx* 2005, 2 (4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, a lack of coordination, and visual impairment, which impact the quality of life of the individual. The clinical course of MS can vary from individual to individual, but invariability of the disease can be categorized in three forms: relapsing-remitting, secondary progressive, and primary progressive.

Studies support the efficacy of fumaric acid esters for treating MS, which are presently undergoing phase II clinical testing (Schimrigk et al., *Eur J Neurology* 2006, 13, 604-610; and Wakkee and Thio, *Current Opinion Investigational Drugs* 2007, 8 (11), 955-962).

Assessment of MS treatment efficacy in clinical trials can be accomplished using tools such as the Expanded Disability Status Scale and the MS Functional as well as magnetic resonance imaging lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis)

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischemic colitis, diversion colitis, Bechet's colitis, and indeterminate colitis.

FAEs are inhibitors of NF-κB activation and therefore may be useful in treating inflammatory diseases such as Crohn's disease and ulcerative colitis (Atreya et al., *J Intern Med* 2008, 263 (6), 59106).

Irritable Bowel Syndrome

Irritable bowel syndrome is a disorder that affects the large intestine and is typically characterized by abdominal pain or cramping, a bloated feeling, flatulence, diarrhea or constipation and/or mucus in the stool.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or by other factors.

As an inhibitor of NF-κB activation and as shown in animal studies (Joshi et al., US 2007/0027076) FAEs may be useful in treating pulmonary diseases such as asthma and chronic obstructive pulmonary disorder.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, *Pharmacological Reviews* 2004, 56 (4), 515-548). The airflow limitation is usually progressive and associated with an abnormal inflammatory response of the lungs to noxious particles and gases. COPD is characterized by a shortness of breath that lasts for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

Neurodegenerative Disorders

Neurodegenerative diseases such as Parkinson's disease, Alzheimer's disease, Huntington's disease and amyotrophic lateral sclerosis are characterized by progressive dysfunction and neuronal death. NF-κB inhibition has been proposed as a therapeutic target for neurodegenerative diseases (Camandola and Mattson, *Expert Opin Ther Targets* 2007, 11 (2), 123-32).

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to control smooth muscle movements and coordinate changes in posture as normal, leading to tremor, incoordination, and slowed, reduced movement (bradykinesia) (Blandini, et al., *Mol. Neurobiol.* 1996, 12, 73-94).

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

Huntington's Disease

Huntington's disease is an autosomal dominant neurodegenerative disorder in which specific cell death occurs in the neostriatum and cortex (Martin, *N Engl J Med* 1999, 340, 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, *N Engl J Med* 2001, 344, 1688-1700). ALS begins with weakness, often in the hands and less frequently in the feet that generally progresses up an arm or leg. Over time, weakness increases and spasticity develops characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

Others

Other diseases and conditions for which compounds of Formula (I) or Formula (II) can be useful in treating include rheumatica, granuloma annulare, lupus, autoimmune carditis, eczema, sarcoidosis, and autoimmune diseases including acute disseminated encephalomyelitis, Addison's disease, alopecia areata, ankylosing spondylitis, antiphospholipid antibody syndrome, autoimmune hemolytic anemia, autoimmune hepatitis, autoimmune inner ear disease, bullous pemphigoid, Bechet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anemia, psoriasis, psoriatic arthritis, polymyositis, primary biliary cirrhosis, rheumatoid arthritis, schizophrenia, scleroderma, Sjogren's syndrome, stiff person syndrome, temporal arteritis, ulcerative colitis, vasculitis, vitiligo, and Wegener's granulomatosis.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

From the foregoing description, various modifications and changes in the compositions and methods disclosed herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds disclosed in this application, may have been generated on an automated basis by use of a commercially available chemical naming software program, and have not been independently verified. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

The invention claimed is:

1. A process for preparing monomethyl fumarate (MMF) or a pharmaceutically acceptable salt thereof; comprising reacting monomethyl maleate with a compound of formula (II)

to produce MMF; wherein $R^1$ is selected from unsubstituted $C_1$-$C_6$ alkyl, unsubstituted $C_3$-$C_6$ cycloalkyl, substituted $C_1$-$C_6$ alkyl and substituted $C_3$-$C_6$ cycloalkyl; and the substitution is selected from halo and $C_1$-$C_6$ alkoxy.

2. The process of claim 1, wherein the reaction occurs in a solvent.

3. The process of claim 2, wherein the solvent is selected from the group consisting of acetonitrile, benzonitrile, hexane, heptane, toluene, xylene, anisole, cumene, chlorobenzene, cyclohexane, methylcyclohexane, ethyl acetate, dichloromethane, dichloroethane, trichloroethane, tetrachloroethane, tetrahydrofuran, diphenyl ether, methyl tert-butyl ether, dioxane, dimethoxyethane, diethoxyethane, dibutyl ether, diisopropyl ether, and combinations thereof.

4. The process of claim 2, wherein the solvent is selected from toluene and acetonitrile.

5. The process of claim 2, wherein the monomethyl maleate and solvent are present in amounts to provide a molar ratio of the monomethyl maleate to solvent in a range of about 1 to 50 to about 1 to 1.

6. The process of claim 1, wherein $R^1$ is selected from Me, Et, n-Pr, i-Pr, n-Bu, i-Bu, sec-Bu, or t-Bu.

7. The process of claim 1, wherein $R^1$ is selected from cyclopropyl or cyclobutyl.

8. The process of claim 1, wherein $R^1$ is Me.

9. The process of claim 1, wherein the monomethyl maleate and $R^1C(O)Cl$ are present in amounts to provide a molar ratio of the monomethyl maleate to $R^1C(O)Cl$ in a range of about 1 to 0.010 to about 1 to 1.

10. The process of claim 9, wherein the molar ratio of the monomethyl maleate to $R^1COCl$ is in a range of about 1 to 0.010 to about 1 to 0.02.

11. The process of claim 1, wherein the $R^1C(O)Cl$ is present in an amount of about 1 to 100 mole % of the amount of monomethyl maleate that is present.

12. The process of claim 1, wherein the reaction occurs at a temperature ranging from about 50° C. to about 100° C.

13. The process of claim 1, wherein the reaction occurs over a period of about 2 to 140 hours.

14. The process of claim 1, wherein the reaction occurs in toluene, the MMF and toluene are present in amounts to provide a molar ratio of the monomethyl maleate to the toluene of about 1 to 3; the compound of formula (II) is acetyl chloride; the reaction occurs (i) in the presence of about 20 mole % of acetyl chloride, (ii) for a period of about 14 hours, and (iii) at a temperature of about 85° C.

15. The process of claim 1, wherein the monomethyl maleate is prepared by reacting maleic anhydride with methanol.

16. The process of claim 15, wherein the reaction of maleic anhydride with methanol occurs in the presence of a solvent.

17. The process of claim 15, wherein the reaction of maleic anhydride with methanol occurs in the absence of a solvent.

18. The process of claim 15, wherein the reaction of maleic anhydride with methanol occurs in a solvent, and the solvent is selected from the group consisting of acetonitrile, benzonitrile, hexane, heptane, toluene, xylene, anisole, cumene, chlorobenzene, cyclohexane, methylcyclohexane, ethyl acetate, dichloromethane, dichloroethane, trichloroethane, tetrachloroethane, tetrahydrofuran, diphenyl ether, methyl tert-butyl ether, dioxane, dimethoxyethane, diethoxyethane, dibutyl ether, diisopropyl ether, and combinations thereof.

19. The process of claim 18, wherein the solvent is selected from toluene and acetonitrile.

20. The process of claim 15, wherein the reaction of maleic anhydride with methanol occurs in a solvent, and the maleic anhydride and solvent are present in amounts that provide a molar ratio of the maleic anhydride to solvent in the range of about 1 to 25 to about 1 to 0.1.

21. The process of claim 15, wherein the maleic anhydride and methanol are present in amounts to provide a molar ratio of the maleic anhydride to methanol of about 1 to 1.2 to about 1 to 1.4.

22. The process of claim 15, wherein the reaction of maleic anhydride with methanol occurs at a temperature from about 15° C. to about 100° C.

23. The process of claim 15, wherein the reaction of maleic anhydride with methanol occurs over a period of about 1 to 140 hours.

24. The process of claim 15, wherein the reaction of maleic anhydride with methanol occurs at a temperature of about 60° C. and over a period of about 3 hours.

25. The process of claim 15, wherein after reacting maleic anhydride with methanol, a resulting reaction mixture is concentrated by removing volatile material from the reaction mixture, and the concentrate is used for the reaction with the compound of formula (II).

26. The process of claim 15, wherein after reacting maleic anhydride with methanol, a resulting reaction mixture is concentrated, by removing volatile material from the reaction mixture, diluted with a solvent, and the solvent diluted concentrate is used for the reaction with the compound of formula (II).

27. The process of claim 25, wherein the volatile material comprises one or more of unreacted methanol and the reaction solvent.

28. The process of claim 26, wherein the volatile material comprises one or more of unreacted methanol and the reaction solvent.

29. The process of claim 15, wherein the steps of (i) reacting maleic anhydride with methanol to form monomethyl maleate; and (ii) reacting the monomethyl maleate with a compound of formula (II) to produce MMF; occur in a single reaction vessel.

30. The process of claim 29, comprising:
    (a) concentrating the monomethyl maleate-containing reaction mixture to obtain a monomethyl maleate concentrate;
    (b) diluting the monomethyl maleate concentrate with a solvent; and
    (c) reacting the solvent-diluted monomethyl maleate concentrate with a compound of formula (II).

31. The process of claim 1, comprising reacting the MMF with a compound of formula (IV) to produce an MMF prodrug of formula (V):

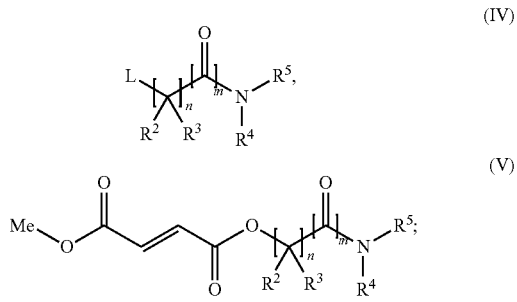

wherein L is a leaving group; each $R^2$ and $R^3$ is independently H, $C_{1-6}$ alkyl, or substituted $C_{1-6}$ alkyl;
each $R^4$ and $R^5$ is independently H, $C_{1-6}$ alkyl, or substituted $C_{1-6}$ alkyl; or
$R^4$ and $R^5$, together with the nitrogen to which they are attached, form a 5-10 membered heteroalkyl ring; m is 0 or 1; and n is an integer from 1 to 6; provided that when m is 0, then n is an integer from 2 to 6.

32. The process of claim 31, wherein L is selected from halo, OH, O-tosylate, and O-mesylate.

33. The process of claim 31, wherein n is 1.

34. The process of claim 31, wherein each $R^2$ and $R^3$ is independently H.

35. The process of claim 31, wherein each $R^4$ and $R^5$ is independently Me, Et, n-Pr, i-Pr, n-Bu, i-Bu, sec-Bu, t-Bu, n-pentyl, or n-hexyl.

36. The process of claim 31, wherein $R^4$ and $R^5$, together with the nitrogen to which they are attached to, form a morpholino, pyrrolidino, or piperidino ring.

37. The process of claim 31, wherein the MMF prodrug is selected from:
    N,N-diethylcarbamoyl)methyl methyl (2E)but-2-ene-1,4-dioate;
    methyl 2-morpholin-4-yl-2-oxoethyl (2E)but-2-ene-1,4-dioate;
    methyl 2-morpholin-4ylethyl (2E)but-2-ene-1,4-dioate;
    methyl 3-morpholin-4-ylpropyl (2E)but-2-ene-1,4-dioate;
    methyl 4-morpholin-4ylbutyl (2E)but-2-ene-1,4-dioate; and
    methyl 5-morpholin-4-ylpentyl (2E)but-2-ene-1,4-dioate;
    and pharmaceutically acceptable salts of any of the foregoing.

38. The process of claim 31, further comprising recrystallizing the MMF prodrug.

39. The process of claim 31, wherein the MMF prodrug is substantially free of toxic impurities.

\* \* \* \* \*